(12) United States Patent
Marogil

(10) Patent No.: US 11,504,134 B2
(45) Date of Patent: Nov. 22, 2022

(54) NON-PNEUMATIC SURGICAL TOURNIQUET

(71) Applicant: MAR-MED INC., Grand Rapids, MI (US)

(72) Inventor: Jerry Paul Marogil, Grand Rapids, MI (US)

(73) Assignee: MAR-MED INC., Grand Rapids, MI (US)

( * ) Notice: Subject to any disclaimer, the term of this patent is extended or adjusted under 35 U.S.C. 154(b) by 351 days.

(21) Appl. No.: 16/338,370

(22) PCT Filed: Sep. 28, 2017

(86) PCT No.: PCT/IB2017/055982
§ 371 (c)(1),
(2) Date: Mar. 29, 2019

(87) PCT Pub. No.: WO2018/060931
PCT Pub. Date: Apr. 5, 2018

(65) Prior Publication Data
US 2020/0022708 A1    Jan. 23, 2020

Related U.S. Application Data

(60) Provisional application No. 62/401,619, filed on Sep. 29, 2016.

(51) Int. Cl.
*A61B 17/132* (2006.01)
*A61B 90/00* (2016.01)
*A61B 17/00* (2006.01)

(52) U.S. Cl.
CPC .......... *A61B 17/1325* (2013.01); *A61B 90/06* (2016.02); *A61B 2017/0046* (2013.01); *A61B 2017/00849* (2013.01); *A61B 2017/00862* (2013.01); *A61B 2017/00889* (2013.01); *A61B 2090/061* (2016.02)

(58) Field of Classification Search
CPC .............. A61B 17/132; A61B 17/1322; A61B 17/1325; A61B 17/1327; A61B 17/135; A61B 17/1355
See application file for complete search history.

(56) References Cited

U.S. PATENT DOCUMENTS 2,882,903 A    4/1959  Ramien
4,991,757 A *  2/1991  Deakyne .............. A47G 25/905
                                                        223/111

(Continued)

OTHER PUBLICATIONS

Extended European Search Report for European Application No. 17855133.9, dated Mar. 16, 2020, 11 pages, Munich, Germany.

*Primary Examiner* — Diane D Yabut
(74) *Attorney, Agent, or Firm* — Stinson LLP

(57) ABSTRACT

A non-pneumatic tourniquet including a tourniquet ring configured to resiliently constrict around a body part of a subject. The tourniquet ring defines a plurality of openings. A handle moves the tourniquet ring onto the body part and includes a first strap having a first end secured to the tourniquet ring at one of the openings and a second end secured to the tourniquet ring at one of the openings. A second strap has a first end secured to the tourniquet ring at one of the openings and a second end secured to the tourniquet ring at one of the openings.

11 Claims, 21 Drawing Sheets

(56) References Cited

U.S. PATENT DOCUMENTS

| | | | |
|---|---|---|---|
| 5,628,329 A * | 5/1997 | Bennett | A61F 5/41 |
| | | | 128/842 |
| D399,568 S | 10/1998 | VanCleave et al. | |
| 5,823,982 A | 10/1998 | Park | |
| 5,873,813 A | 2/1999 | Weiss | |
| 6,117,069 A * | 9/2000 | Vollrath | A61F 5/41 |
| | | | 600/38 |
| D478,170 S | 8/2003 | Catlett | |
| D611,143 S | 3/2010 | Williams et al. | |
| D624,246 S | 9/2010 | Houtz | |
| D648,440 S | 11/2011 | Allen | |
| D685,094 S * | 6/2013 | Green | A61B 17/132 |
| | | | D24/188 |
| D733,306 S | 6/2015 | Blankenship | |
| D759,829 S | 6/2016 | Ben Noon | |
| 2005/0049630 A1 | 3/2005 | Ambach | |
| 2005/0080450 A1 * | 4/2005 | Gavriely | A61B 17/1322 |
| | | | 606/201 |
| 2006/0138181 A1 * | 6/2006 | Thom | A47G 25/905 |
| | | | 223/111 |
| 2008/0275499 A1 * | 11/2008 | Brackett | A61B 17/1322 |
| | | | 606/203 |
| 2009/0248061 A1 * | 10/2009 | Gavriely | A61B 17/1355 |
| | | | 606/201 |
| 2011/0022077 A1 * | 1/2011 | Green | A61B 17/132 |
| | | | 606/203 |
| 2015/0342614 A1 | 12/2015 | Gavriely et al. | |
| 2016/0128700 A1 | 5/2016 | Fry | |
| 2018/0140506 A1 | 5/2018 | Smith et al. | |

* cited by examiner

FIG. 14

NON-PNEUMATIC SURGICAL TOURNIQUET

FIELD

The present disclosure generally relates to non-pneumatic surgical tourniquets.

BACKGROUND

A tourniquet is a constricting or compressing device, used to control venous and arterial circulation to an extremity for a period of time. Tourniquets are commonly used in orthopedic surgical procedures and enable surgeons to work in a bloodless operative field by preventing blood flow to an extremity. With better visibility, tourniquets allow surgical procedures to be performed with improved precision, safety and speed.

Tourniquets can be pneumatic (gas pressured constriction) or non-pneumatic (mechanical or elastic pressured constriction). But pneumatic tourniquets have become nearly standard in surgical procedures for a number of years. A pneumatic tourniquet system typically involves three components; an inflatable cuff, a compressed gas source, and an instrument that monitors and controls cuff pressure. In order to use a pneumatic tourniquet effectively, blood must first be expelled from the extremity. This is typically accomplished with elastic pressure by wrapping an esmarch bandage around the limb proximally toward the body. Once an esmarch bandage is wrapped to the desired location and the cuff in place, the cuff can be inflated to the pressure required to occlude the vessels and prevent further blood flow to the surgical site.

Despite advantages of the pneumatic systems, such as providing accurate pressure monitoring, there are notable disadvantages to pneumatic tourniquets as well. Primarily, pneumatic systems are costly in large part due to the need for equipment and instrumentation to provide and measure pressure. The investment required for this type of equipment can be substantial for less developed countries and independent clinician practices. But even the cuffs used in pneumatic systems can be quite costly. Refurbished cuffs may reduce the cost per use, but depend on additional handling of contaminated materials.

Additionally, effective use of pneumatic systems can be somewhat demanding. Using an esmarch bandage to expel venous blood and a separately inflated cuff to prevent arterial circulation involves multiple steps. The equipment and tubes associated with pneumatic systems is obtrusive, and requires the technical knowledge and skill of often multiple operators from start to finish. The cuffs are made to be wide in order to disperse high pressure over greater surface area and reduce nerve or other tissue injury. However, inflation can pinch or irritate skin and their high profile can be obstructive of the surgical site. Moreover, pneumatic systems can be painful to wear and may cause nerve injury to the wearer.

Considering these factors of pneumatic tourniquet use, non-pneumatic tourniquets have recently gained traction in the market again. Non-pneumatic tourniquets are generally made with an elastic material that provides compression by stretching or through manually tightening. They are simple, low cost, and easily disposable due to the lack of need for associated electronic equipment. Non-pneumatic tourniquets can expel venous blood and occlude arterial circulation in one quick step.

However, there exists a need for a tourniquet system which is reasonably priced, low profile, and easy to use

SUMMARY

In one aspect, a non-pneumatic tourniquet generally comprises a tourniquet ring configured to resiliently constrict around a body part of a subject. The tourniquet ring defines a plurality of openings. A handle moves the tourniquet ring onto the body part and includes a first strap having a first end secured to the tourniquet ring at one of the openings and a second end secured to the tourniquet ring at one of the openings. A second strap has a first end secured to the tourniquet ring at one of the openings and a second end secured to the tourniquet ring at one of the openings.

In another aspect, a method of exsanguinating a body part of a subject and constricting vessels of the body part to limit blood flow to the body part generally comprises manipulating a compression ring of a non-pneumatic tourniquet to position the compression ring over a distal end portion of the body part. The compression ring comprises a flat band of resiliently elastic material. Applying a force to a handle of the tourniquet attached to the compression ring to slide the tourniquet proximally along the body part as the compression ring constricts around the body part to exsanguinate the body part and constrict vessels of the body part to prevent blood flow through the body part without changing an axial orientation of the compression ring.

In yet another aspect, a non-pneumatic tourniquet generally comprises a compression ring comprising a band of resiliently elastic material extending circumferentially around a ring axis for exsanguinating a body part of a subject and constricting vessels of the body part. The compression ring has a proximal end, a distal end, and a height extending between the proximal end and the distal end along the ring axis. The compression ring also has an inner surface, an outer surface, and a radial thickness extending between the inner and outer surfaces. The radial thickness is substantially uniform about the circumference of the compression ring. A handle is separately attached to the compression ring.

BRIEF DESCRIPTION OF THE DRAWINGS

FIG. 14 is an elevation of another embodiment of a tourniquet ring;

Corresponding reference characters indicate corresponding parts throughout the drawings.

DESCRIPTION OF THE PREFERRED EMBODIMENTS

Figure 1:
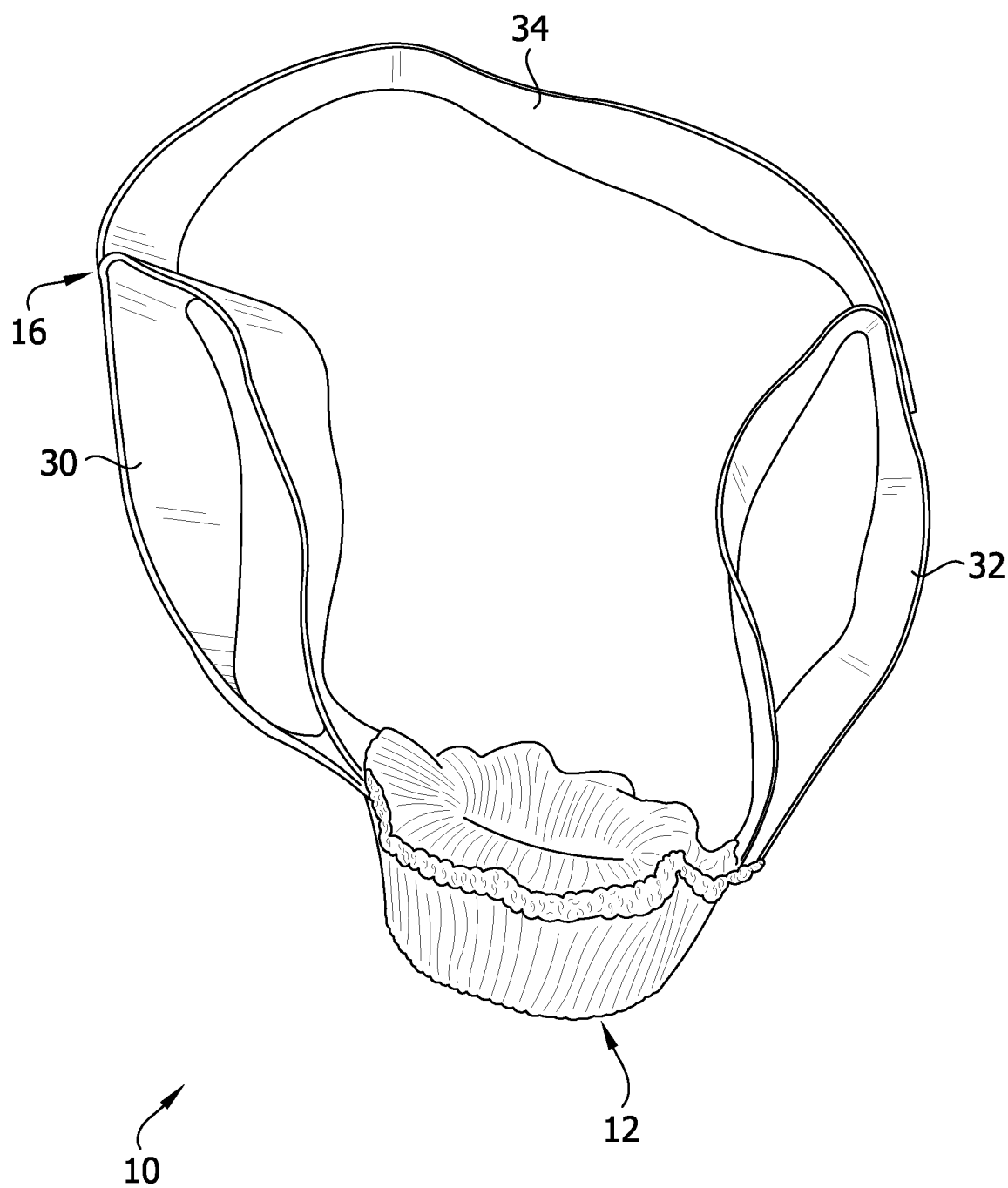
FIG. 1 is a perspective of a tourniquet.
Figure 2:
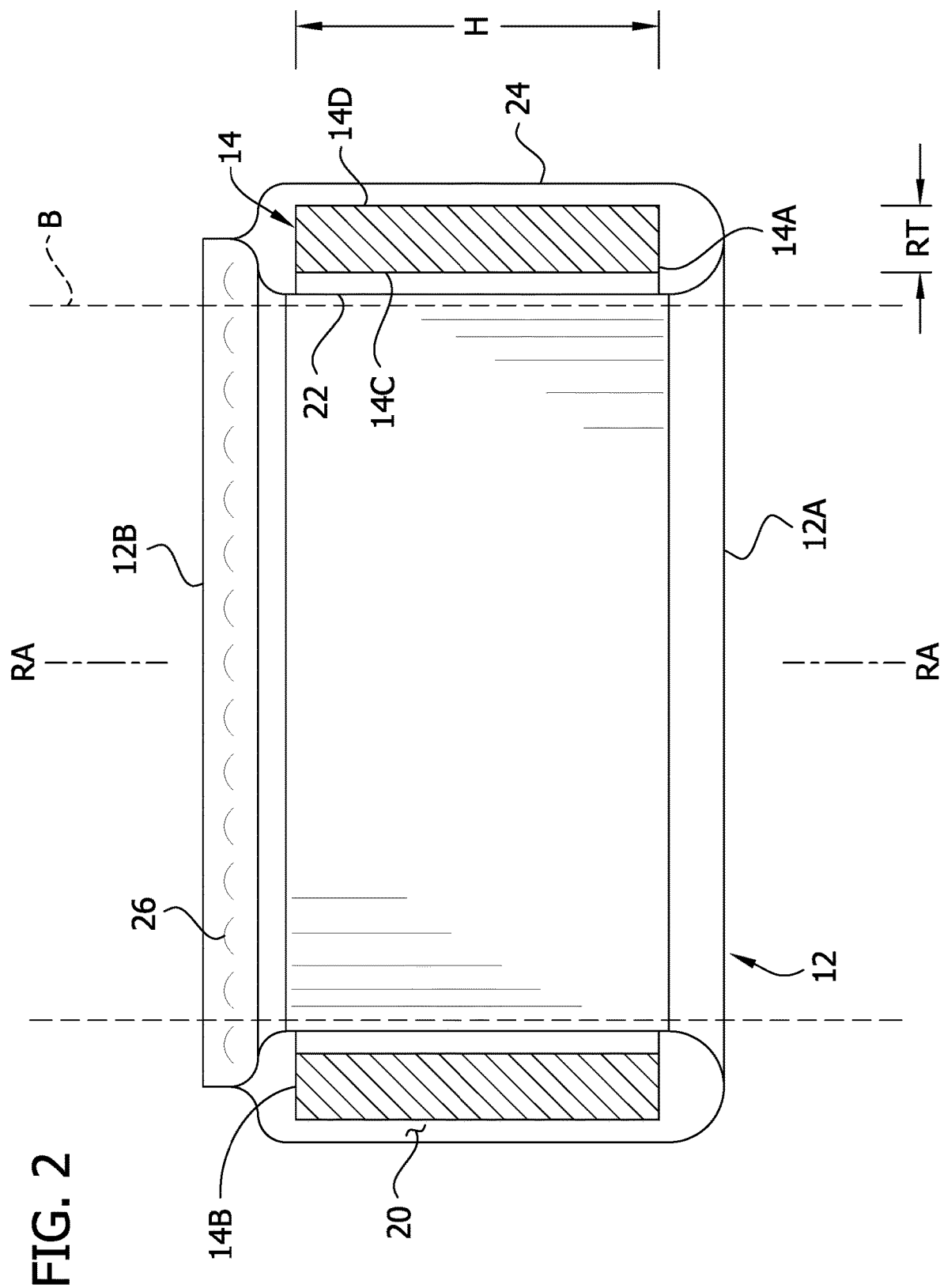
FIG. 2 is a cross-section of a cover and a compression ring of the tourniquet.

Referring to FIGS. 1 and 2, one embodiment of a non-pneumatic tourniquet is generally indicated at reference number 10. The tourniquet 10 includes an annular cover, generally indicated at 12, and an elastic compression ring, generally indicated at 14, which is received in the annular cover. A handle, generally indicated at 16, is attached to the cover 12 for pulling the tourniquet 10 onto a body part B of a subject (e.g., a human or animal surgical patient). Suitably, the tourniquet 10 is sized for a particular type of body part B (e.g., a portion of a limb) and may be configured to operatively restrict blood flow to any body part of that type within a normal size range (i.e., the tourniquet may be a one-size-fits-all device). In the illustrated embodiment, the tourniquet 10 is configured to operatively engage the arm of a patient to restrict blood flow to a distal portion of the arm. Other embodiments of tourniquets may be configured to operatively engage and restrict blood flow at other body parts such as legs, etc. The tourniquet 10 may suitably be made of inexpensive materials that can be manufactured, packaged in sterile packaging, and delivered to a treatment site, such as an operating room. As will be apparent, the tourniquet 10 may have a relatively narrow profile to minimize the size of the segment of the body part B that is covered by the tourniquet in use, and thereby maximize the size of the surgical field. As explained below, the handle 16 allows a user to pull the tourniquet 10 over the body part B of the subject using a one-hand or two-handed grip. And as the tourniquet 10 is pulled over the body part B, the cover 12 slides along the body part and the compression ring 14 exsanguinates the body part without twisting within the cover. Once the tourniquet 10 is properly positioned, it constricts tightly around a segment of the body part B to restrict blood flow to the portions of the body part extending distally from the constricted segment. Suitably, the tourniquet 10 is configured to impart sufficient pressure on the body part B to overcome venous blood pressure as it is pulled onto the body part, thereby exsanguinating the body part; likewise the tourniquet is configured to impart sufficient pressure on the body part to overcome arterial blood pressure at least when it is properly positioned on the body part, thereby restricting new blood flow to the surgical site after the tourniquet is placed.

The annular cover 12 may be formed from one or more sheets of flexible material that are assembled into a toroidal shape. Although the following discussion describes a cover 12 that is formed of a fabric, it will be understood that other flexible sheet material such as film, foil, felt, etc. may also be used without departing from the scope of the disclosure. In the illustrated embodiment, the cover 12 is sized and arranged to loosely conform to the shape of the compression ring 14. That is, the radial and axial dimensions of an interior 20 of the cover 12 are somewhat larger than the non-stretched dimensions of the compression ring 14. The circumferential size of the annular cover 12 may also be somewhat larger than the compression ring 14 so that the cover scrunches to generally conform to the circumferential dimensions of the compression ring when the compression ring is not stretched. This allows the cover 12 to expand circumferentially without stretching the fabric.

Referring to FIG. 2, the cover 12 includes an inner panel 22 and an outer panel 24 that are joined together at a distal end margin 12A and a proximal end margin 12B of the cover and define the cover interior 20. In the illustrated embodiment, the inner and outer panels 22, 24 of the cover 12 are formed from a single piece of fabric that is folded over at the distal end margin 12A. Thus, the inner and outer panels 22, 24 are "joined together" at the distal end margin 12A of the cover 12 by being formed from a unitary piece of fabric. The inner and outer panels may also be separately joined together at the distal end margin of the cover in other embodiments. The proximal end margins of the inner and outer panels 22, 24 are sewn together by one or more threads 26, but may also be joined together in other ways (e.g., by being bonded together with an adhesive, by being formed from a single piece of fabric that is folded over the compression ring at the proximal end margin, etc.) without departing from the scope of the disclosure. Further, the cover 12 can be formed from two separate pieces of material joined together in a suitable fashion without departing from the scope of the disclosure.

The fabric used to construct the cover 12 allows the compression ring 14 to expand circumferentially as it is pulled over the body part B of the subject. Exemplary fabric materials for the cover 12 include a combination of spandex and one or more of polyester, rayon, cotton, etc. Other materials or combinations of materials may also be used without departing from the scope of the disclosure. In one or more embodiments, the fabric is circumferentially stretchable. For example, the fibers used to form the cover fabric (e.g., knitted fibers, woven fibers, etc.) can be arranged to have slack in the circumferential direction, which allows the fabric to expand circumferentially when stretched. That is, the fabric may be arranged to stretch circumferentially through straitening of the fibers that are oriented in the circumferential direction of the cover 12, which allows stretching of the fabric without requiring stretching of the constituent fibers. The fabric may be substantially less stretchable in the axial direction of the cover 12 than in the circumferential direction. For example, the constituent fibers can be arranged to have less slack in the axial direction than the circumferential direction. As explained below, using a cover 12 that is substantially non-stretchable in the axial direction allows the handle 16 to transmit a positioning force to the compression ring 14 through the annular cover 12. Suitably, the fabric used for the cover 12 has a low coefficient of friction with the body part B of the subject (e.g. human skin, etc.). This allows the tourniquet 10 to slide over the body part B during placement with minimal frictional resistance. As explained below, however, a low friction sleeve (not shown) may also be used in combination with the tourniquet to improve sliding. The configuration of the tourniquet to slide along the body part B provides a different mechanism for donning the tourniquet than other non-pneumatic tourniquets which are rolled on a body part.

Figure 3:
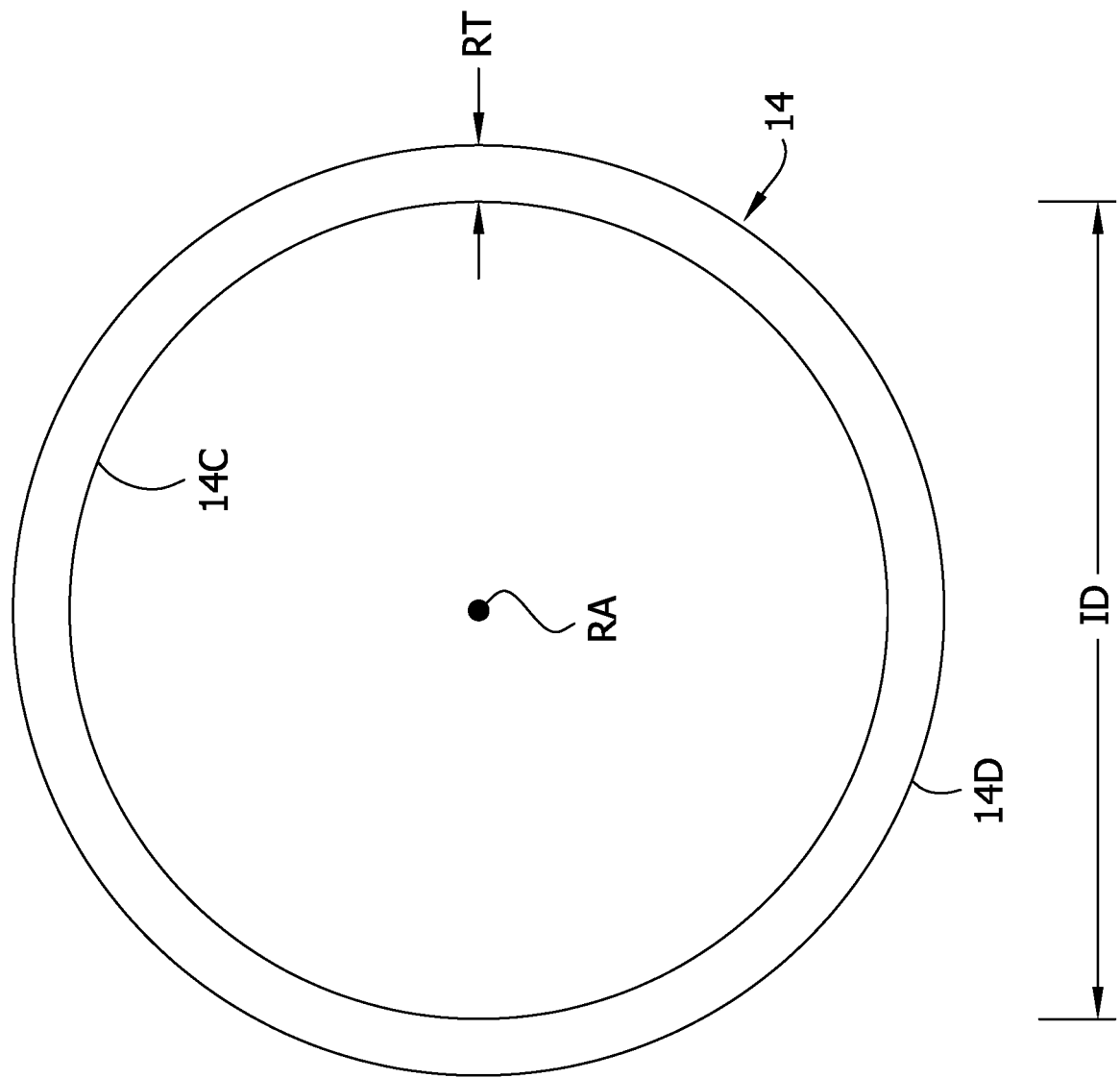
FIG. 3 is a top plan view of the compression ring.

The compression ring 14 comprises a band of resiliently elastic material that extends circumferentially around a ring axis RA. The illustrated compression ring 14 has a rectangular cross-sectional shape when taken through a vertical section as shown in FIG. 2, and a circular shape when viewed from a top of the ring as shown in FIG. 3. However, compression rings of other shapes may also be used in other embodiments. Although the compression ring 14 has a uniform tubular shape in the non-stretched configuration, it is conformable to the cross-sectional shape of the body part B in use. The compression ring 14 may comprise a continuous band of elastic material. In other words, the compression ring may be seamless. For example, the compression ring 14 may comprise a segment cut from a seamless, extruded tube of resiliently elastic material. The compression ring 14 may suitably comprise a nylon. However, other resiliently elastic materials may also be used without departing from the scope of the invention. As will be seen in some of the following embodiments, the compression ring 14 may have openings for attaching a handle, however, the compression ring will still be considered to have a uniform tubular shape.

The compression ring 14 can be sized and arranged to constrict around a relatively short axial segment of a body part B. Referring to FIG. 2, the compression ring 14 has a distal end 14A, a proximal end 14B, and a height H extending between the distal and proximal ends along the ring axis RA. The height H of the compression ring 14 may suitably be in a range of from about 2 cm to about 4 cm. The relatively short height H of the compression ring 14 minimizes the size of the segment of the body part B that the tourniquet 10 covers during use to maximize the size of the blood-restricted portion of the body part (e.g., the surgical site).

The compression ring 14 is sized and arranged to provide a sufficient resiliently compressive force when stretched around the body part B to restrict blood flow. Referring to FIG. 3, the compression ring 14 has an inner surface 14C and an outer surface 14D. The inner surface 14C defines a non-stretched inner diameter ID of the compression ring 14. The non-stretched inner diameter ID of the compression ring 14 may suitably be less than the effective outer diameter of a body part B so that the compression ring must be stretched circumferentially to be pulled onto the body part. The required stretching may be accomplished by radially expanding the tourniquet 10 before placing it on the body part B or by manipulating the tourniquet and the body part to stretch the compression ring 14 over the distal end portion of the body part. After being stretched, the compression ring 14 resiliently returns toward its non-stretched configuration and constricts around the body part B to restrict blood flow. A radial thickness RT extends between the inner and outer surfaces 14C, 14D of the compression ring 14. The radial thickness RT of the compression ring 14 is selected based on the material of the ring to provide sufficient elastic compression strength to restrict blood flow when the ring 14 resiliently constricts around the body part B. In one or more embodiments, the radial thickness RT of the compression ring 14 may be in a range of from about 0.25 cm to about 0.3 cm.

As shown in FIGS. 2 and 3, the illustrated compression ring 14 has a flat and uniform cross-section. The radial thickness RT of the compression ring 14 is substantially uniform along the height H of the compression ring 14 as shown in FIG. 2; the radial thickness RT of the compression ring 14 is likewise substantially uniform about the circumference of the compression ring as shown in FIG. 3. The uniform, flat thickness RT of the compression ring 14 allows the tourniquet 10 to be pulled onto the body part B of the subject without causing the compression ring 14 to twist endwise within the cover 12 or otherwise changing the axial orientation of the compression ring with respect to the body part B during pulling. Thus, the ring 14 is configured so that it does not roll onto the body part B. In embodiments where openings are formed in the compression ring 14 to attach a handle, the compression ring will still be considered to have a uniform thickness along the height H and about the circumference at least everywhere material of the compression ring is present.

Referring again to FIG. 1, the handle 16 defines a plurality of handle loops that provide multiple grasping configurations for pulling or pushing the tourniquet 10 onto the body part B. The handle 16 includes a first loop strap 30 that is secured to the cover 12 at a first circumferential position and a second loop strap 32 that is secured to the cover at a second circumferential position spaced apart from the first circumferential position. In the illustrated embodiment, the first and second loop straps 30, 32 are positioned at diametrically opposite positions about the cover 12. Although the loop straps may also be secured to the cover in other ways, the illustrated loop straps 30, 32 are sewn to the proximal end margin 12B of the cover 12. More specifically, each loop strap 30, 32 has first and second end portions that are sewn together and to the cover 12 at the respective circumferential position. Thus, the first loop strap 30 defines a first handle loop and the second loop strap 32 defines a second handle loop that is spaced apart from the first handle about the cover 12. In the illustrated embodiment, the first and second handle loops are about the same size, but they may also be different sizes without departing from the scope of the invention. As explained below, the first and second handle loops may be separately grasped by two hands when pulling or pushing the tourniquet 10 onto the body part B. The first and second loop straps may also be arranged in other ways to form the first and second handle loops. For example, the end portions of each loop strap may be secured to the cover at circumferentially spaced apart positions, or a middle portion of a loop strap may be secured to the cover while the end portions of the loop straps are secured together remote from the cover. Still other arrangements are also possible including other handle designs shown and described in other embodiments of the disclosure.

In the illustrated embodiment, the compression ring 14 and the cover 12 together form a tourniquet ring. In other embodiments, a tourniquet ring may not include a cover or may only include a partial cover, etc. Thus, it will be understood that the handle may be secured to a tourniquet ring without being secured to a cover in certain embodiments (e.g., by being secured directly to a compression ring). For example, in one or more embodiments (some of which are described in greater detail below), the tourniquet ring is uncovered and used in combination with a lubricant to reduce friction when sliding axially along the body part of the subject. It is understood that a lubricant may also be used in combination with the tourniquet 10 to reduce friction and enhance sliding without departing from the scope of the disclosure.

A connecting strap 34 is secured to the first loop strap 30 and the second loop strap 32 to connect the first and second loop straps and form at least a portion of a third handle loop. The connecting strap 34 has first and second end margins. The first end margin of the connecting strap 34 is secured to the first loop strap 30 at a location remote from the cover 12

(e.g., at roughly a midpoint of the first loop strap), and the second end margin of the connecting strap is secured to the second loop strap 32 at a location remote from the cover (e.g., at roughly a midpoint of the second loop strap). The connecting strap 34 could also be secured to either or both of the first and second loop straps 30, 32 at other points along the lengths thereof. In the illustrated embodiment, the end margins of the connecting strap 34 are sewn onto the loop straps, but the connecting strap may also be secured to the loop straps in other ways in other embodiments. As shown in FIG. 1, the connecting strap 34 is connected between the first and second loop straps 30, 32 such that the first and second loop straps form respective portions of the third handle loop. That is, the first and second loop straps 30, 32, connect the connecting strap 34 to the cover 12 to form the third handle loop. The third handle loop is larger than the first and second handle loops, which allows a user to grasp the handle 16 at a position more remote from the compression ring 14 than is possible using the first and second handle loops. For example, the connecting strap 34 can be grasped with one hand to position the tourniquet 10 on the body part B of a subject. In one embodiment, a clinician may grasp the connecting strap 34 to position the tourniquet 10 on the subject's body part B. In one embodiment, a subject may grasp the connecting strap 34 to pull the tourniquet 10 with one arm onto his or her own opposite arm. The handle 16 may have other configurations without departing from the scope of the disclosure.

Figure 4:
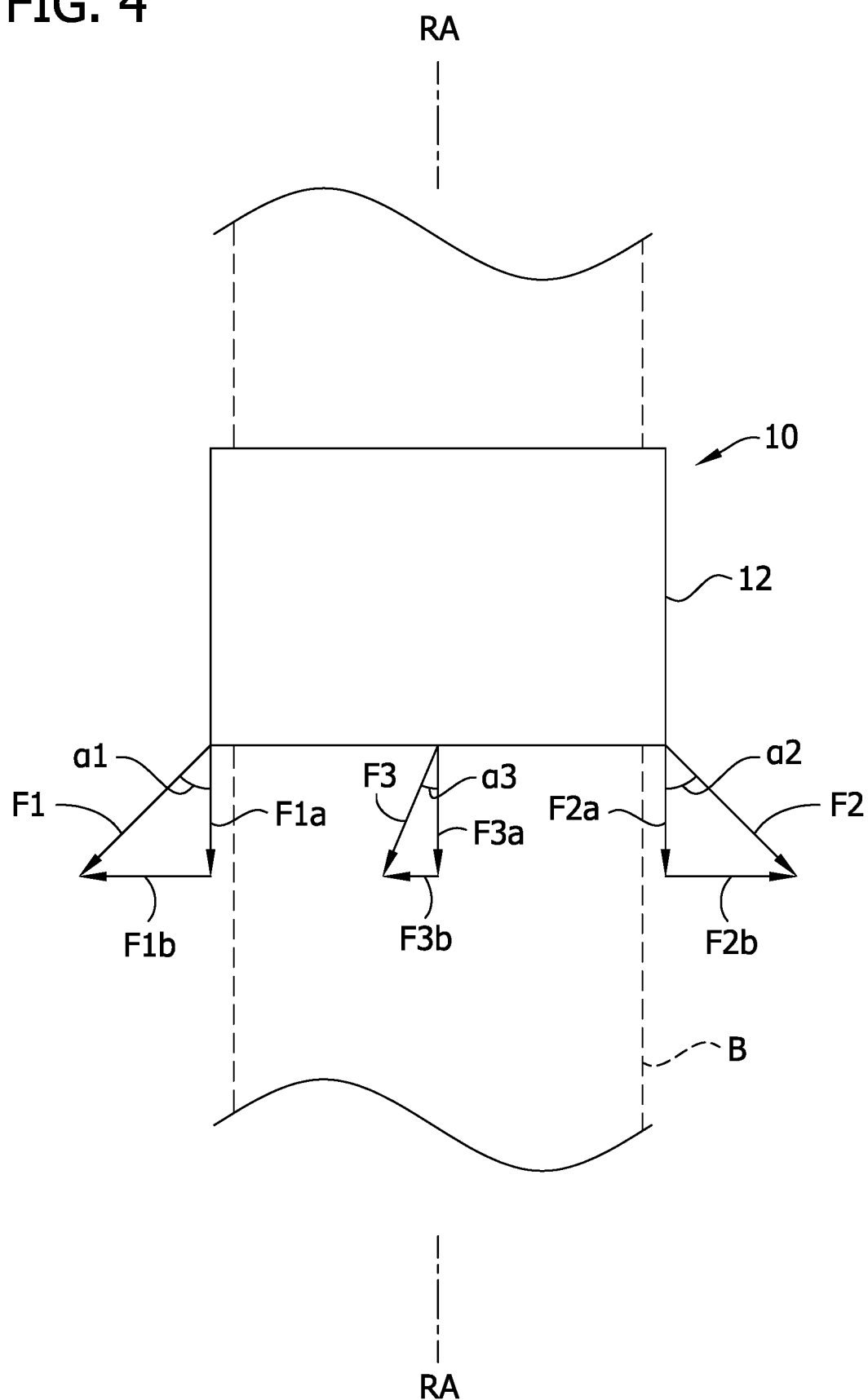
FIG. 4 is a schematic diagram illustrating forces acting on the tourniquet 10 in use.

In general, the tourniquet 10 is positioned by sliding the tourniquet ring onto the body part B along the ring axis RA. Thus, to effectively pull or push the tourniquet onto the body part B, the pulling or pushing forces (generically, positioning forces) should be concentrated along the ring axis RA. To grip any of the first, second, and third handle loops while pulling or pushing the tourniquet onto a body part B without interfering with the body part, the handle loops must be angled outward with respect to the ring axis RA. FIG. 4 schematically illustrates the orientation of the positioning forces F1, F2, F3 imparted on the cover 12 using the first, second, and third handle loops respectively. It is understood that the first and second positioning force vectors F1, F2 illustrated in FIG. 4 represent the forces imparted on the cover 12 in a first angular orientation about the ring axis RA and the third positioning force vector F3 represents the positioning force imparted on the cover 12 in a second angular orientation rotated 90° about the ring axis RA with respect to the first angular orientation.

Each of the positioning forces F1, F2, F3 is oriented at a respective angle $\alpha 1$, $\alpha 2$, $\alpha 3$ with respect to the ring axis RA. Because third handle loop provides a grip location that is spaced apart from the tourniquet ring by a greater distance than the grip locations of the first and second handle loops, the pulling angle $\alpha 3$ between the third handle loop and the ring axis RA is smaller than pulling angles $\alpha 1$, $\alpha 2$ between the first and second handle loops and the ring axis RA. The positioning force F1, F2, F3 on each handle loop includes a first component F1a, F2a, F3a oriented parallel to the ring axis RA and a second component F1b, F2b, F3b oriented perpendicular to the ring axis RA. As can be seen, the third handle loop functions better than either of the first and second handle loops when pulling the tourniquet 10 using only one hand because the parallel component F3a is much greater in proportion to the positioning force F3 than for the positioning forces F1, F2 (i.e., F3a/F3>F1a/F1; F3a/F3>F2a/F2). In addition, since the third handle loop is connected to the cover 12 by the first and second loop straps 30, 32, pulling with one hand applies the positioning force F3 to the tourniquet ring at diametrically spaced locations about the body part B for relatively balanced pulling. When two hands are available to pull tourniquet 10, the first and second handle loops can be used effectively because the perpendicular components F1b, F2b of the first and second positioning forces F1, F2 offset one another, and the parallel components F1a, F2a combine to provide a strong positioning force along the ring axis RA. The net force acting on the cover 12 is oriented generally along the ring axis RA. Tourniquet 10 can be applied using two hands in the same manner as shown for tourniquet 10. Similar forces may be applied using the other handle designs shown and described in the disclosure.

An exemplary method of using the tourniquet 10 will now be briefly described. As discussed above, the tourniquet 10 may be configured as a one-time use device. In one embodiment, a user receives the tourniquet 10 in sterile packaging and must remove the packaging before positioning the tourniquet. In certain embodiments, the user places a low friction sleeve (not shown) over the body part B before placing the tourniquet 10 (e.g., a sleeve comprising a silk fabric or other fabric having a low coefficient of friction). In other embodiments, the user places the tourniquet 10 on the body part B without using a sleeve to reduce friction. If the user is able to position the tourniquet 10 using two hands for tourniquet, the user may cut away the connecting strap 34 of tourniquet 10. This may prevent the connecting strap from becoming an impediment during placement.

Initially, the user manipulates the tourniquet 10 and the body part B to stretch the compression ring 14 and cover 12 over the distal end portion of the body part B (e.g., the hand of a subject may be contorted to fit inside of the opening of the tourniquet). If only one hand is available to place the tourniquet 10, the user can grasp the connecting strap 34 and pulls the handle 16 to impart a positioning force F3 on the cover 12. If two hands are available, the user grasps the loop straps 30, 30', 32, 32' and pulls the handle 16 to impart two positioning forces F1, F2 on the cover. The user can also grasp and pull on the first loop strap 30, 30' and the second loop strap 32, 32' in alternating fashion to "walk" the tourniquet 10 distally along the body part B. Because the cover 12, 12' is substantially non-stretchable along the ring axis RA, the positioning force(s) F1, F2, F3 act to slide the cover 12, 12' along the body part B or low friction sleeve. The compression ring 14 maintains its axial orientation as it travels with the cover 12 along the body part B. That is, the proximal end 14B remains forward of the distal end 14A in the direction of travel, and the compression ring does not twist end-over-end within the cover 12. During pulling, the compression ring 14 imparts a radially compressive force on the body part B to exsanguinate the body part. When the tourniquet 10 reaches the desired positon, the compression ring 14 constricts around a segment of the body part B to restrict blood flow.

As indicated above, in one or more methods of using the tourniquet 10 or a tourniquet that includes an exposed (i.e., uncovered) elastic ring, a lubricant is used to facilitate sliding the tourniquet along the body part B. In an exemplary method, after placing a drape over the subject that isolates the surgical field and exposes the body part B, a user may apply a lubricant to the body part and/or the inside surface of the tourniquet ring. Suitably, the lubricant may comprise a surgical antiseptic material for reducing the likelihood of infection, sepsis, or putrefaction. Exemplary lubricant materials include Hibiclens®, sold by Mölnlycke Health Care AB of Gothenburg, Sweden and ChloraPrep® sold by Becton, Dickinson and Company of Franklin Lakes, N.J.

Before or after the lubricant dries, or is otherwise wiped away, the user applies the tourniquet 10 to the body part B as described above. In addition to (optionally) providing an antiseptic treatment of a surgical site prior to a surgical procedure, the lubricant provides a lubricated interface between the tourniquet ring and the body part B, thereby reducing frictional resistance to sliding.

Figure 5:
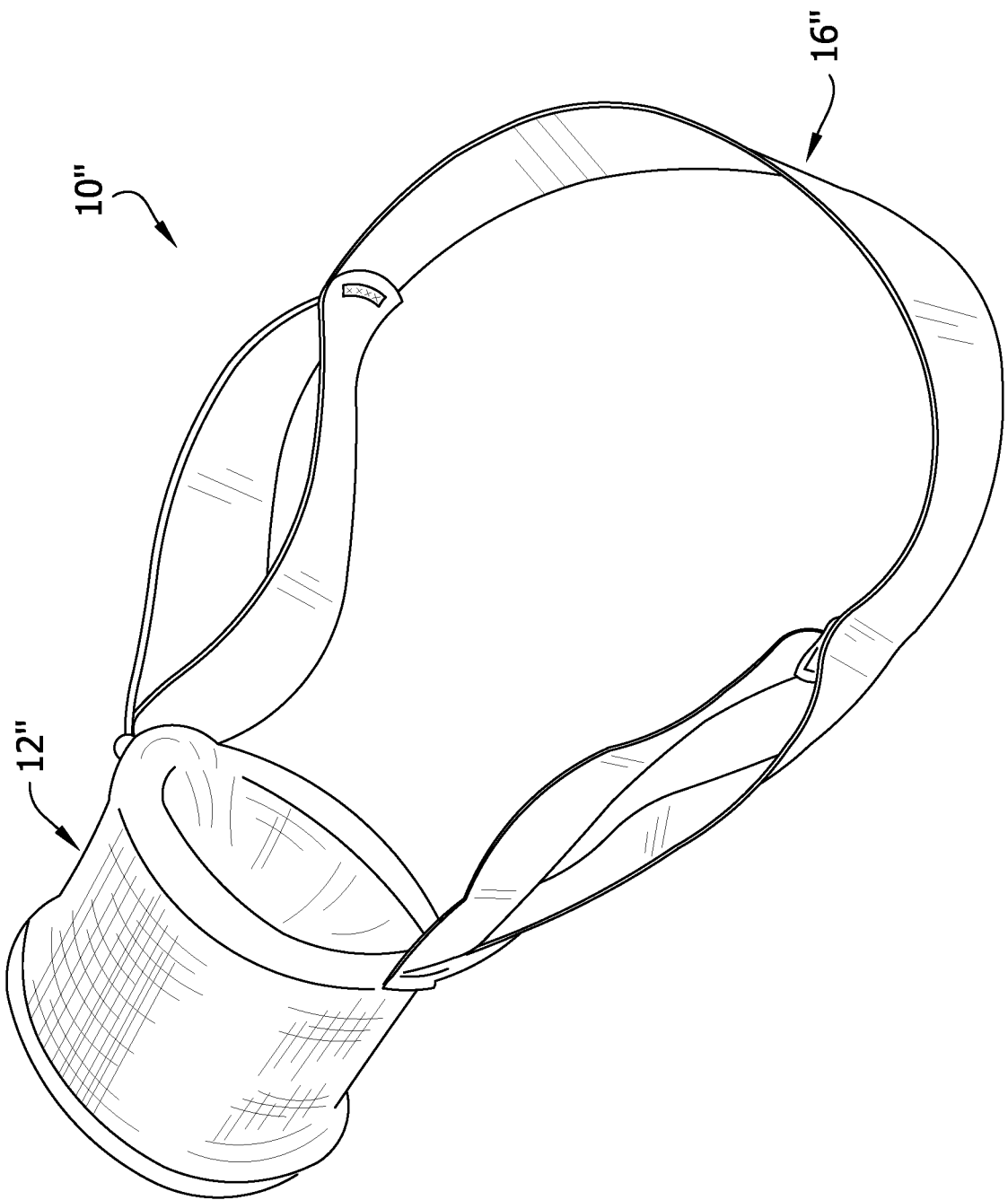
FIG. 5 is a perspective of another embodiment of a tourniquet.

Referring to FIG. 5, a tourniquet 10" of an alternate embodiment is illustrated. The tourniquet 10" is similar to tourniquet 10 except that in tourniquet 10", the distal end of cover 12" includes stitching, the proximal end of the cover defines a fold, and a different type of material is used to form handle 16". The tourniquet otherwise functions the same as tourniquet 10.

Figure 6:
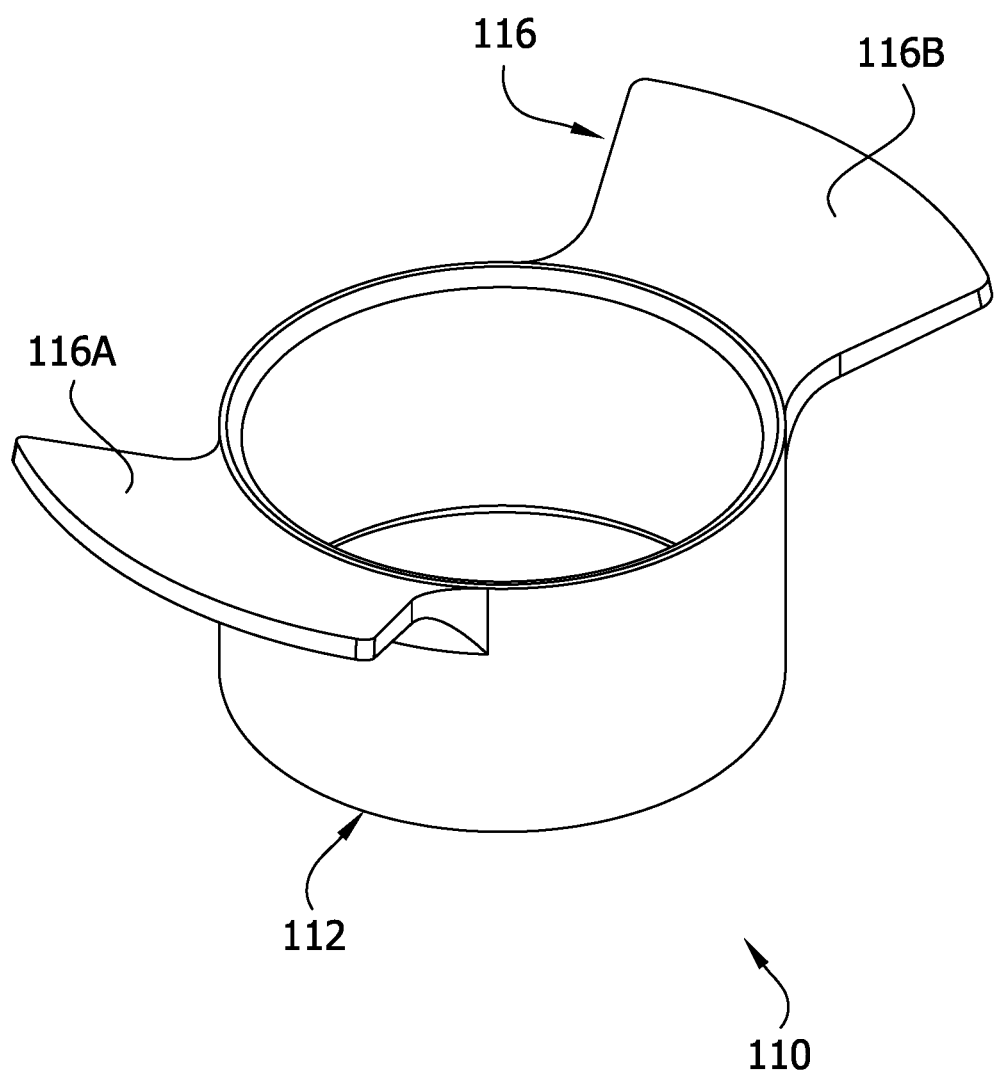
FIG. 6 is a perspective of another embodiment of a tourniquet.

Referring to FIG. 6 another embodiment of a surgical tourniquet is generally indicated at 110. Like tourniquets 10, 10" discussed above, tourniquet 110 includes a tourniquet ring 112 and a handle 116. Unlike tourniquets 10, 10" discussed above, the handle 116 is formed integrally with the tourniquet ring 112 from one piece of material. For example, in a suitable embodiment, the tourniquet ring 112 and the handle 116 are formed integrally from an elastic material such as silicone. Other materials may also be used without departing from the scope of the disclosure. In the illustrated embodiment, the tourniquet ring 112 is uncovered and is configured to be pulled or pushed onto the body portion B of the subject using a lubricant. The tourniquet may also be pulled or pushed onto the body portion B without using a lubricant. In other embodiments, the tourniquet 110 could be used in combination with a textile cover without departing from the scope of the disclosure.

The handle 116 includes first and second handle projections 116A, 116B that project generally radially outwardly from the proximal end portion of the tourniquet ring 112. Application of force to the handle projections 116A, 116B is transferred to the tourniquet ring 112 for pulling or pushing the tourniquet 110 onto the body portion B. In the illustrated embodiment, a width of each handle projection 116A, 116B gradually increases as the projection extends away from the tourniquet ring. The flared handle projections 116A, 116B provide a wide gripping surface for grasping the handle 116. However, the handle projections 116A, 116B could have other configurations without departing from the scope of the disclosure. In the illustrated embodiment, the handle projections 116A, 1116B have free ends that are not connected to one another. In other embodiments, the handle projections can be connected to form a loop or can form individual loops that can optionally be connected by an intermediate length of material as described above in reference to the handle 16. In other embodiments, knobs (not shown) could be molded with the tourniquet ring 112 providing a handle structure for pushing or pulling the tourniquet onto the body.

Figure 7:
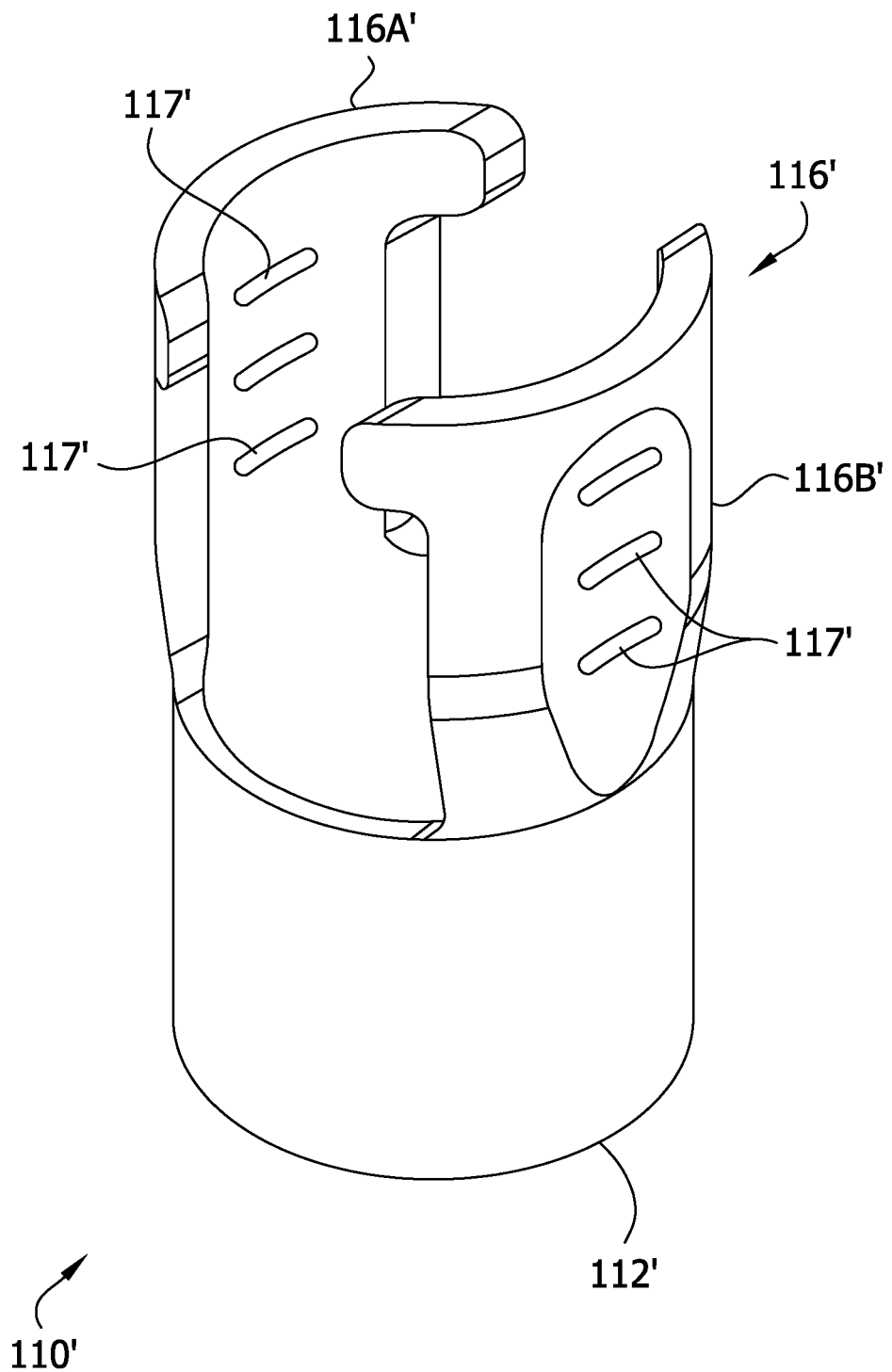
FIG. 7 is a perspective of another embodiment of a tourniquet.
Figure 8:
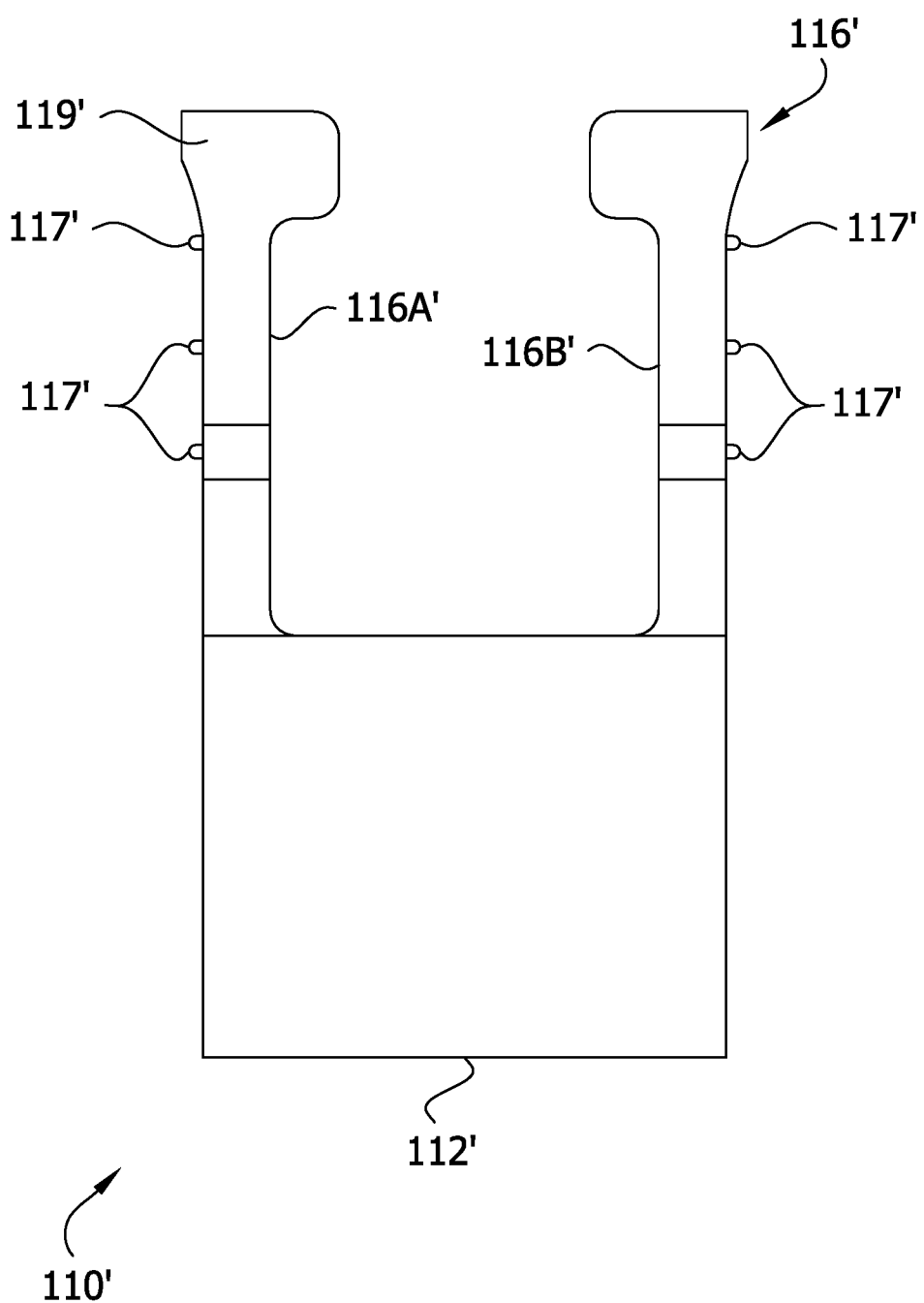
FIG. 8 is an elevation of the tourniquet of FIG. 7.
Figure 9:
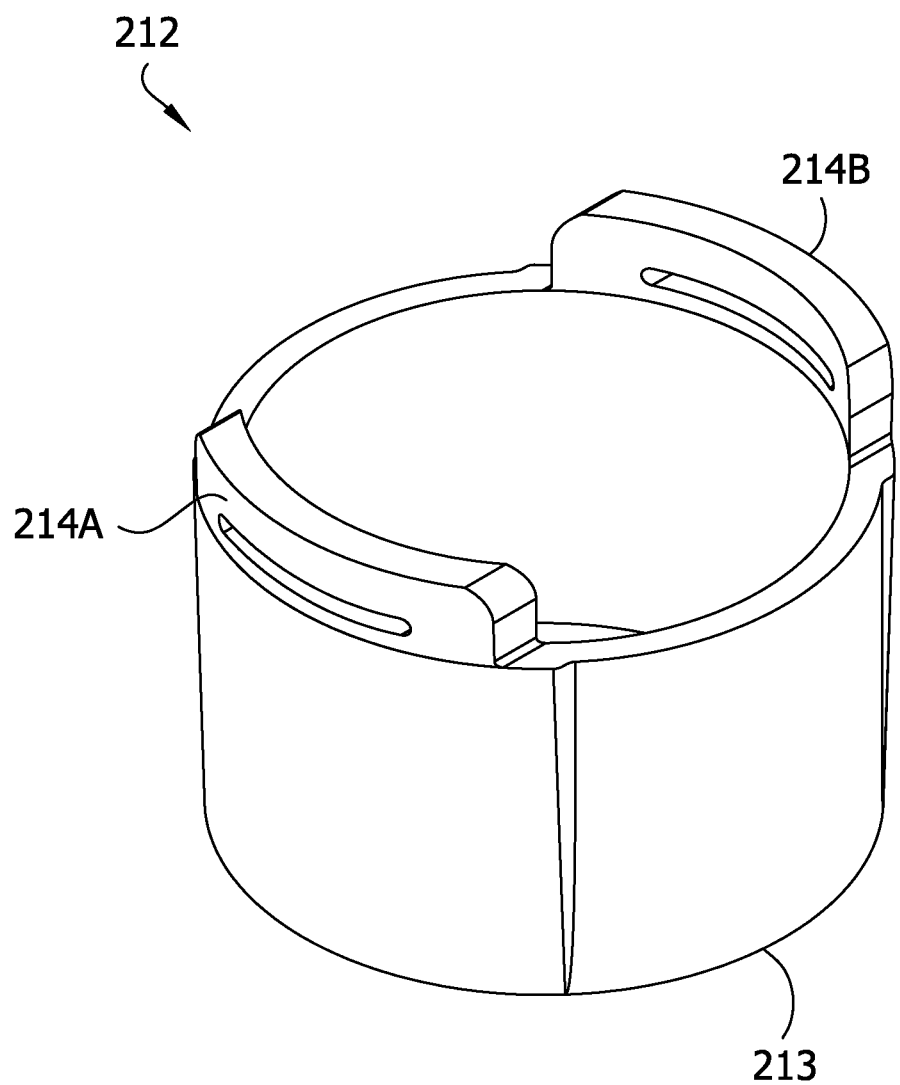
FIG. 9 is a perspective of a tourniquet ring of another embodiment of a tourniquet.
Figure 10:
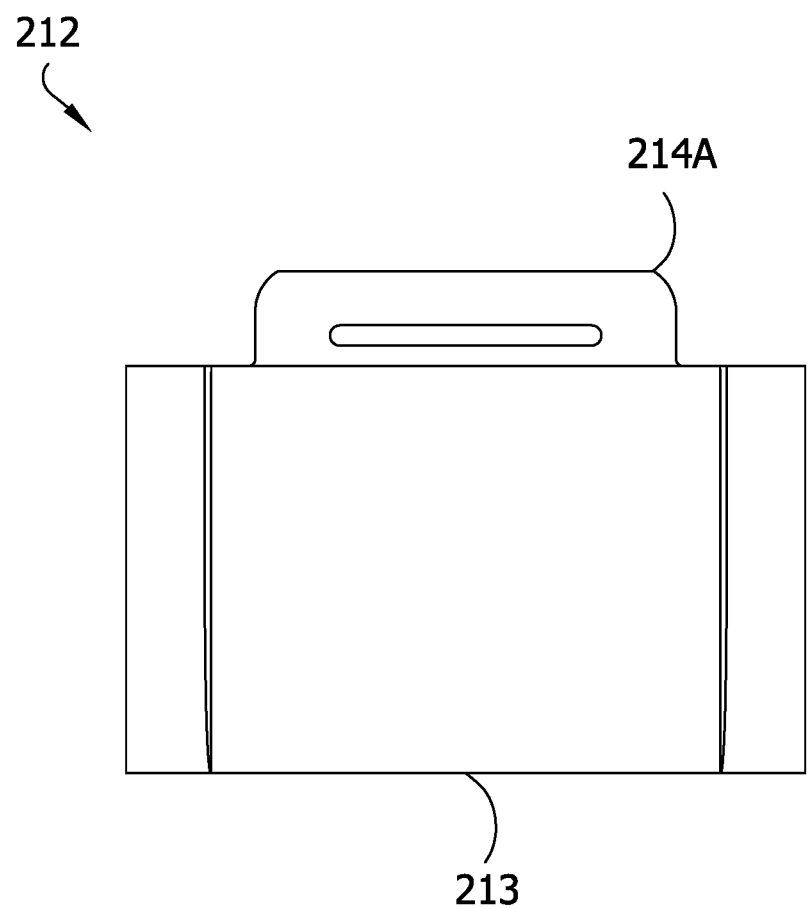
FIG. 10 is an elevation of the tourniquet ring of FIG. 9.
Figure 11:
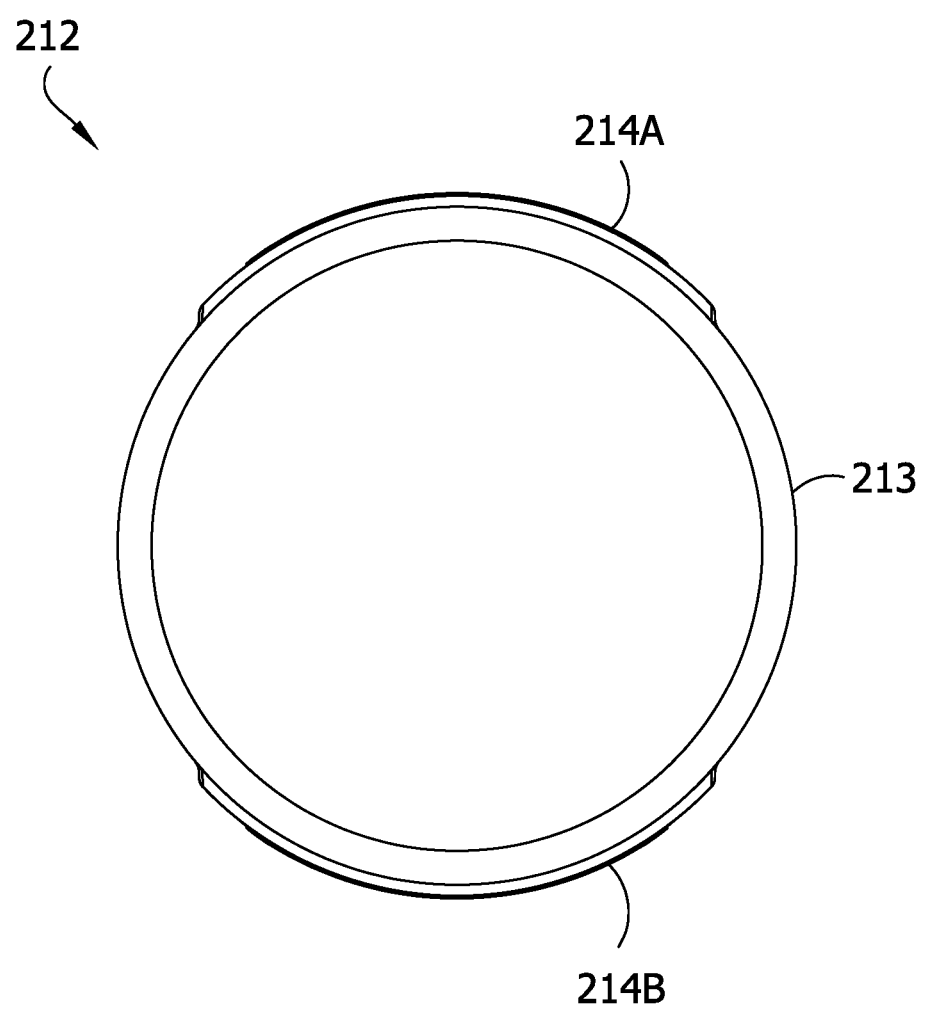
FIG. 11 is a bottom plan view of the tourniquet ring of FIG. 9.
Figure 12:
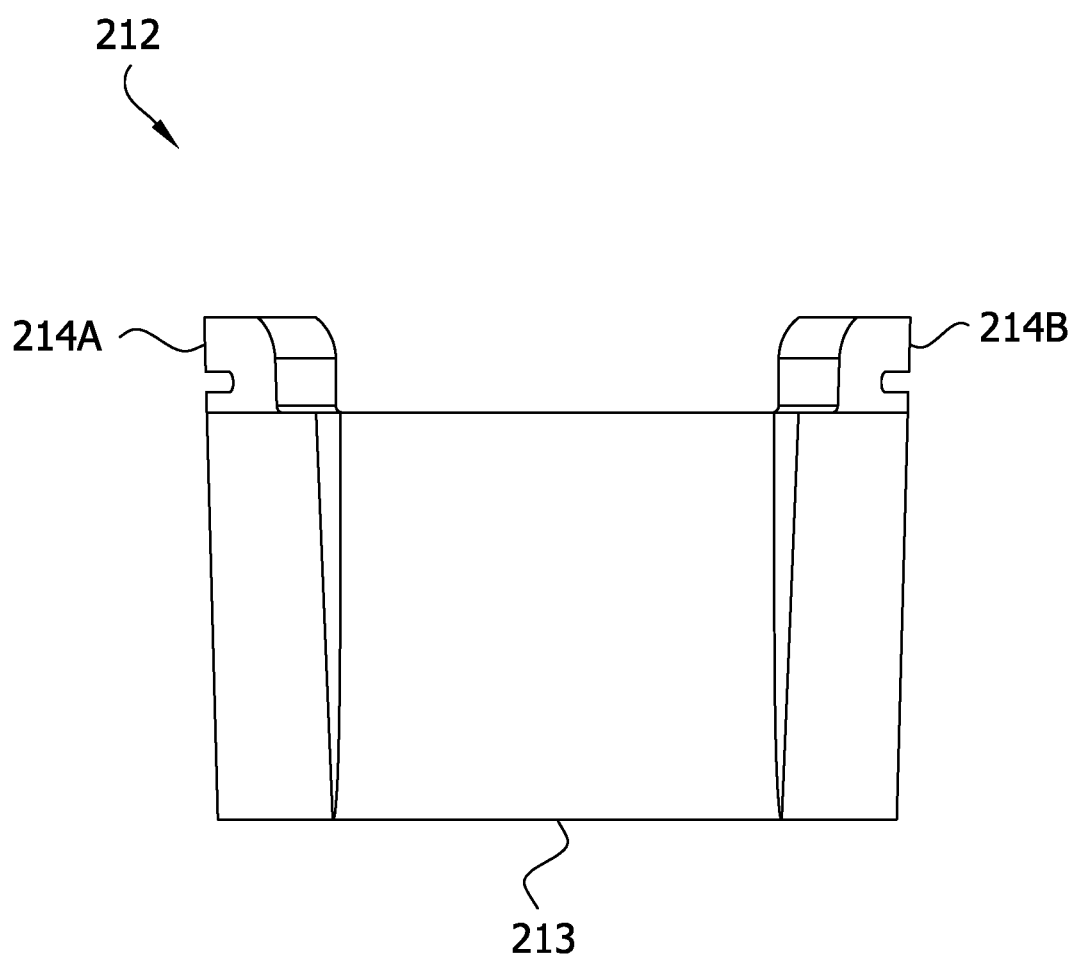
FIG. 12 is another elevation of the tourniquet ring of FIG. 9.

Referring to FIGS. 7-8, another embodiment of a tourniquet is generally indicated at 110'. The tourniquet 110' is similar to the tourniquet 110, and like features are given like reference numbers, plus a prime symbol. Like the tourniquet 110, the tourniquet 110' includes a tourniquet ring 112' and a handle 116' comprising handle projections 116A', 116B' formed integrally with the tourniquet ring from one piece of material. In the illustrated embodiment, however, the handle projections 116A', 116B' extend generally axially when they are not being pulled by a user. Moreover, the handle projections 116A', 116B' include integral gripping formations that are thought to enhance a user's grip of the tourniquet 110' when positioning it on a body part B. For example, gripping ribs 117' project from the radially inward and outward facing surfaces of the handle projections 116A', 116B' to provide additional gripping structure. In addition, the top end portion of each of the handle projections 116A', 116B' includes an outwardly extending gripping flange 119' (FIG. 8). Handle projections may include other gripping formations without departing from the scope of the invention. As shown in FIG. 13A, the handle projections 116A', 116B' are bendable with respect to the tourniquet ring 112' to allow the handle projections to be pulled radially outwardly during placement of the tourniquet 110'.

Referring to FIGS. 9-12, embodiments of another tourniquet are generally indicated at reference number 210. The tourniquet 210 includes a tourniquet ring 212, 212A adapted to impart an elastically compressive load on a body part B of a subject operative to restrict blood flow through the body part. The tourniquet ring 212, 212A includes an elastic ring portion 213, 213A that has an annular shape. As above, the elastic ring portion 213, 213A may be formed from any suitable elastic material such as silicone. In addition to the elastic ring portion 213, the illustrated tourniquet ring 212 includes first and second handle connection loops 214A, 214B that are joined to the elastic ring portion (FIGS. 9-12). The handle connection loops 214A, 214B are adapted to be connected to a handle, generally indicated at 216 in FIG. 13, and described in further detail below. In use, the handle connection loops 214A, 214B are configured to transmit a pulling or pushing force from the handle 216 to the elastic ring portion 213 of the tourniquet ring 212, whereby the tourniquet 210 slides along the body part B in the direction of the force.

Figure 13:
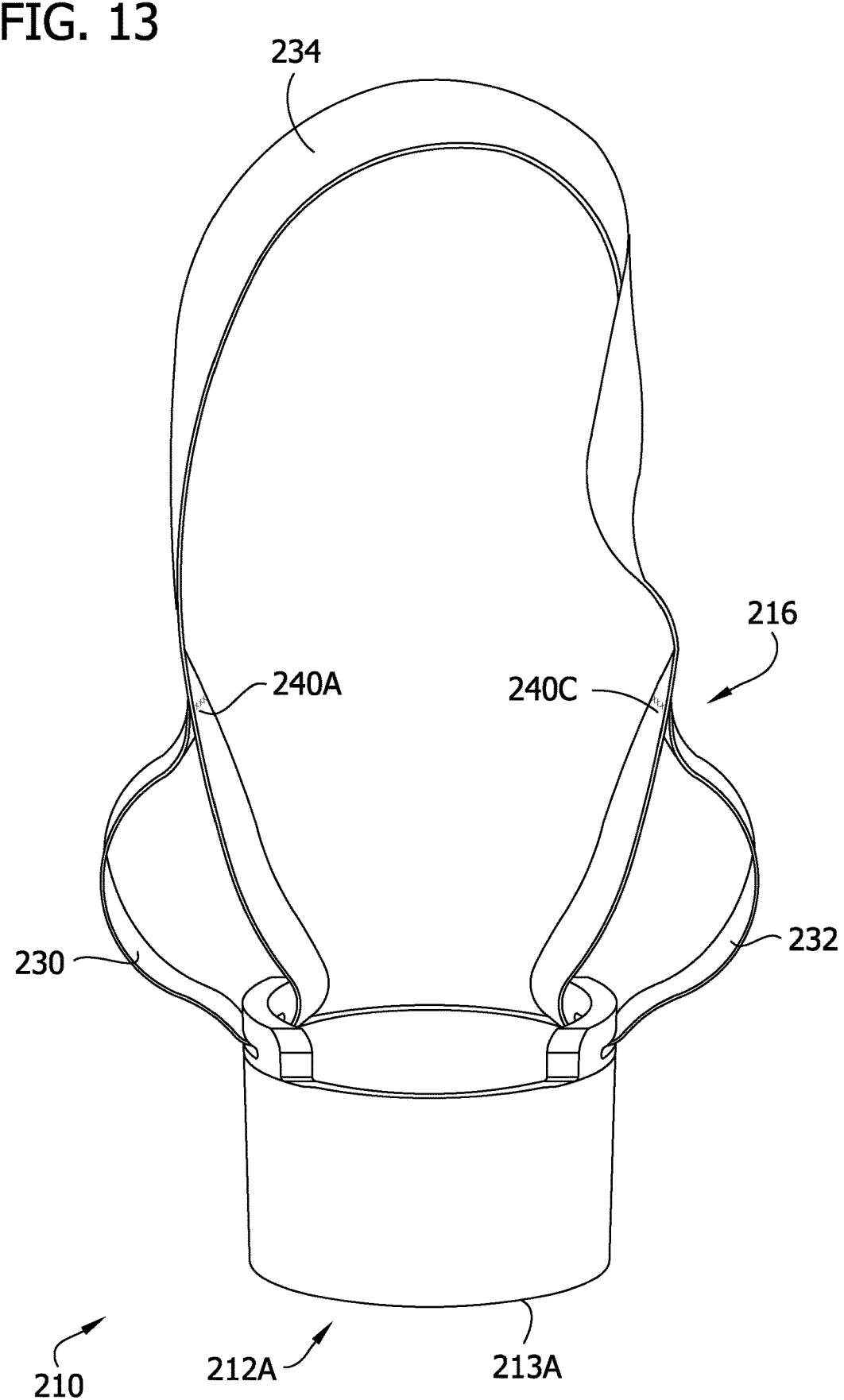
FIG. 13 is a perspective of another tourniquet with a handle operatively attached to a tourniquet ring of the tourniquet.

It is noted that the tourniquet ring 212 shown in FIGS. 9-12 has a different construction than the tourniquet ring 212A shown in FIG. 13. In particular, tourniquet ring 212A in FIG. 13 does not include the handle connection loops 214A, 214B. Instead, the handle 216 is attached to the tourniquet ring 212A by slots in the elastic ring portion 213A. It will be understood that the handle 216 can be attached to the tourniquet ring 212 shown in FIGS. 9-12 by extending portions of the handle through slots in the handle connection loops 214A, 214B. Other handles can be attached to the tourniquet ring 212 without departing from the scope of the disclosure.

In one or more embodiments, the handle connection loops 214A, 214B are joined to the tourniquet ring 212 through co-injection molding. Thus, the handle connection loops 214A, 214B and the tourniquet ring 212 can be formed of materials that are compatible for co-injection molding. Suitably, the materials of the handle connection loops 214A, 214B and the tourniquet ring 212 form a strong bond in the co-injection molding process that can withstand the pulling/pushing forces transmitted between the handle connection loops and the tourniquet ring.

Suitably, the handle connection loops 214A, 214B in FIGS. 9-12 are formed from a more rigid material than the elastic ring portion 213. Using a more rigid material is thought to minimize stretching of the handle connection loops 214A, 214B in the direction of the pulling or pushing force and thus more effectively transmit the pulling or pushing force to the tourniquet ring 212. For example, in one or more embodiments, the elastic ring portion 213 is formed from a silicone or other like material and the handle connection loops 214A, 214B are formed from a higher durometer silicone or another more rigid material such as a thermoplastic. In one embodiment the elastic ring portion 213 is formed from a 30 durometer silicone, and the handle connection loops 214A, 214B are formed from an 80 durometer silicone. Still other materials may be used for the handle connection loops 214A, 214B. In one or more embodiments, a cover (not shown) is removably attached to the tourniquet ring 212, 212A. The cover may be similar to the cover 12 shown in the first embodiment.

Referring to FIG. 13, in one embodiment, the handle 216 is formed from a pliable but substantially non-stretchable fabric. The illustrated handle 216 includes first and second loop straps 230, 232 and a connecting strap 234 extending therebetween. The first and second loop straps 230, 232 and the connecting strap 234 may be used to position the tourniquet 210 on the body part B in the same way as described above in reference to the first and second loop straps 30, 32 and the connecting strap 34 of the tourniquet 10. The first and second loop straps 230, 232 are arranged so that a radially outboard segment of each projects radially outward with respect to the tourniquet ring 212A, making the loops straps easier to grasp in use. The handle 216 further includes first and second strap connection loops 236A, 236B. The first and second strap connection loops 236A, 236B are connected to the first and second loop straps 230, 232, respectively. Each strap connection loop 236A, 236B extends through a slot formed in the elastic ring portion 213A (or slots in the respective handle connection loops 214A, 216B in FIG. 9) and extends circumferentially around the upper portion of the elastic ring portion 213A (or the respective handle connection loops) to connect that handle to the tourniquet ring 212, 212A.

In one or more embodiments the handle 216 may be formed from a single ribbon of elongate fabric (not shown) having a first end portion, a second end portion, and a length extending therebetween. To form the handle 216, the first end portion of the ribbon is inserted through the slot in the first handle connection loop 214A (or a first slot in the elastic ring portion 213A as shown in FIG. 13). The first end portion is subsequently attached (e.g., by sewing, etc.) to an intermediate portion of the ribbon to form a joint 240A, which defines a boundary between the first loop strap 230 and the connecting strap 234. A portion of the ribbon located adjacent to and outboard of the first handle connection loop 214A (or elastic ring portion 213A as shown in FIG. 13) is attached (e.g., by sewing) at a joint 240B to another portion of the ribbon located adjacent to and inboard of the first handle connection loop (or elastic ring portion 213A) to form the first strap connection loop 236A. The second end portion of the ribbon is likewise inserted through the slot in the second handle connection loop 214B (or a second slot in the elastic ring portion 213A as shown in FIG. 13). The second end portion is subsequently attached (e.g., by sewing, etc.) to an intermediate portion of the strip to form a joint 240C, which defines a boundary between the second loop strap 232 and the connecting strap 234. A portion of the ribbon located adjacent to and outboard of the second handle connection loop 214B (or elastic ring portion 213A as shown in FIG. 13) is attached (e.g., by sewing) at another joint 240D to another portion of the ribbon located adjacent to and inboard of the second handle connection loop (or elastic ring portion 213A) to form the second strap connection loop 236B. Suitably, the ribbon is threaded through the first and second handle connection loops 214A, 214B (or slots in the elastic ring portion 213A) and attached to itself such that the outboard segments of ribbon extending between the joints 240A, 240B and 240C, 240D, respectively, are longer than the inboard segments of the ribbon extending between the same pairs of joints. This causes the first and second handle loops 230, 232 to project radially outwardly to make them easier to grasp in use. The handle 216 can also be formed in other ways without departing from the scope of the invention.

Figure 14:
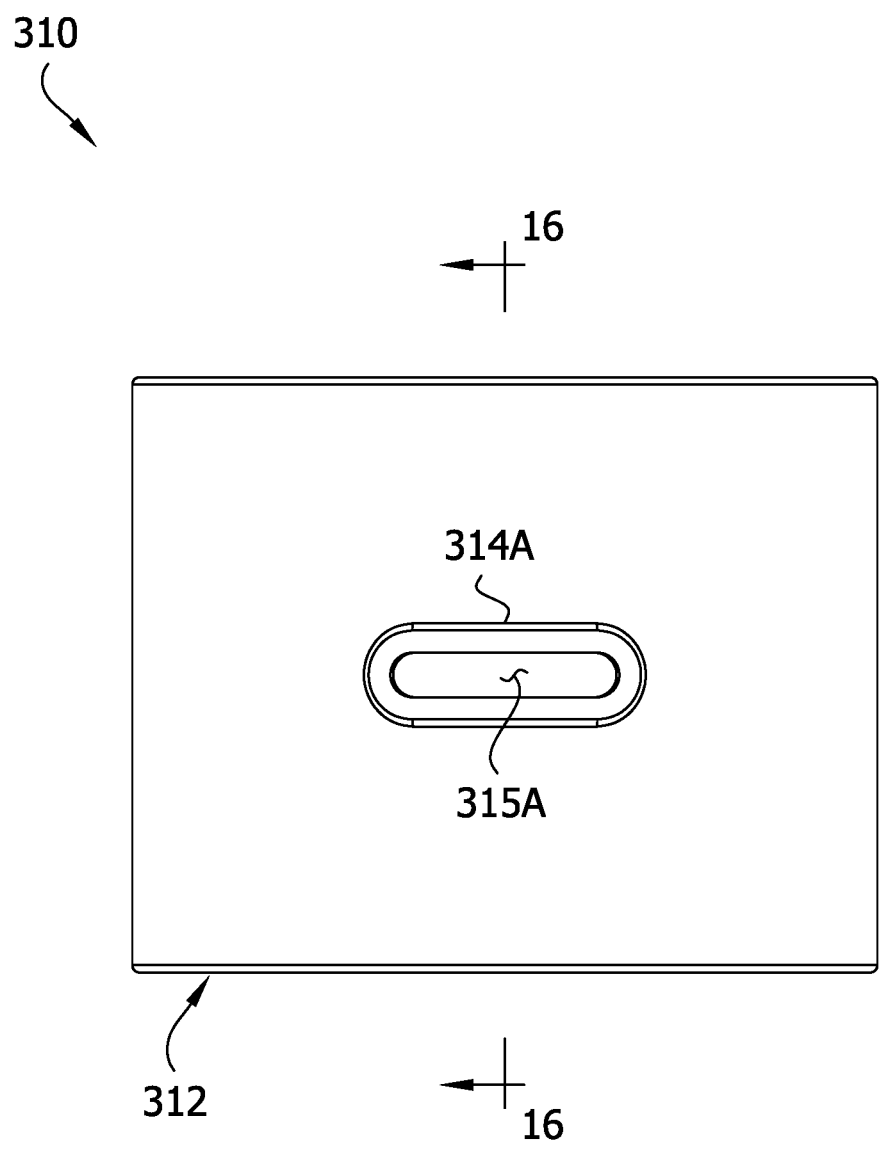
Figure 15:
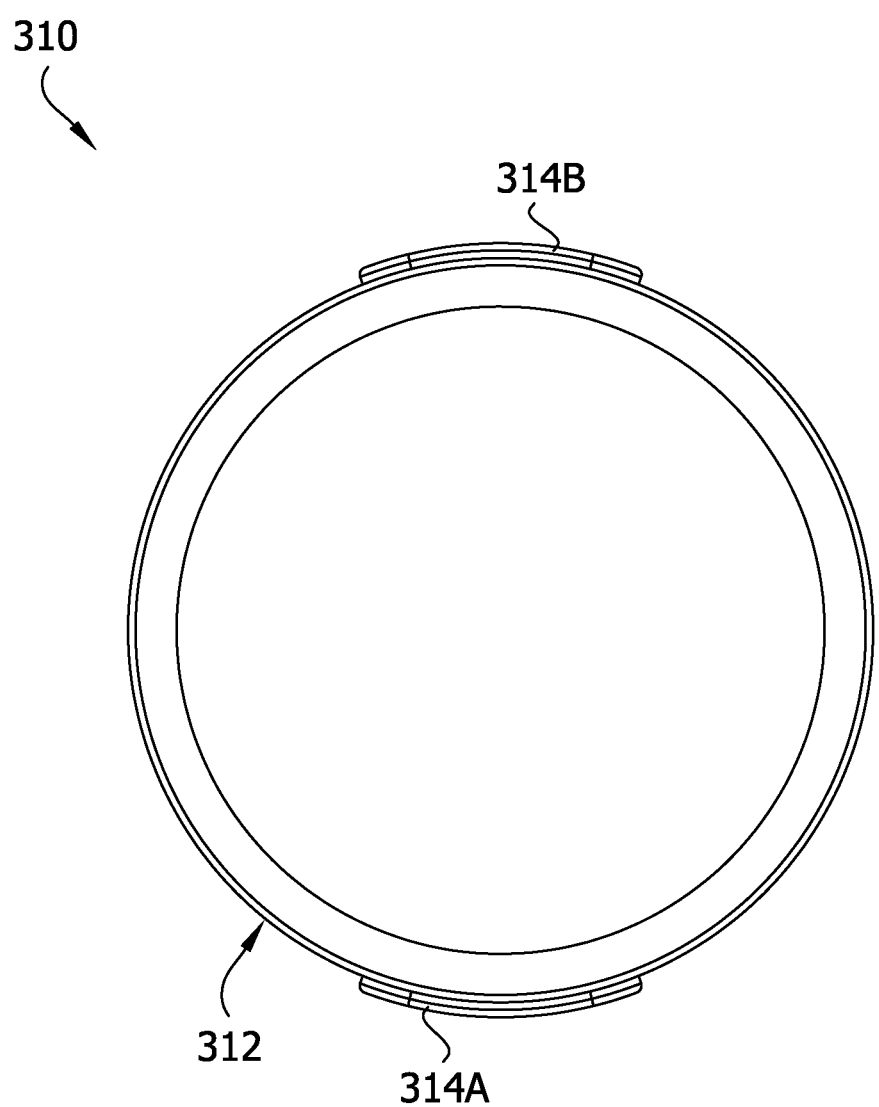
FIG. 15 is a top plan view of the tourniquet ring of FIG. 14.
Figure 16:
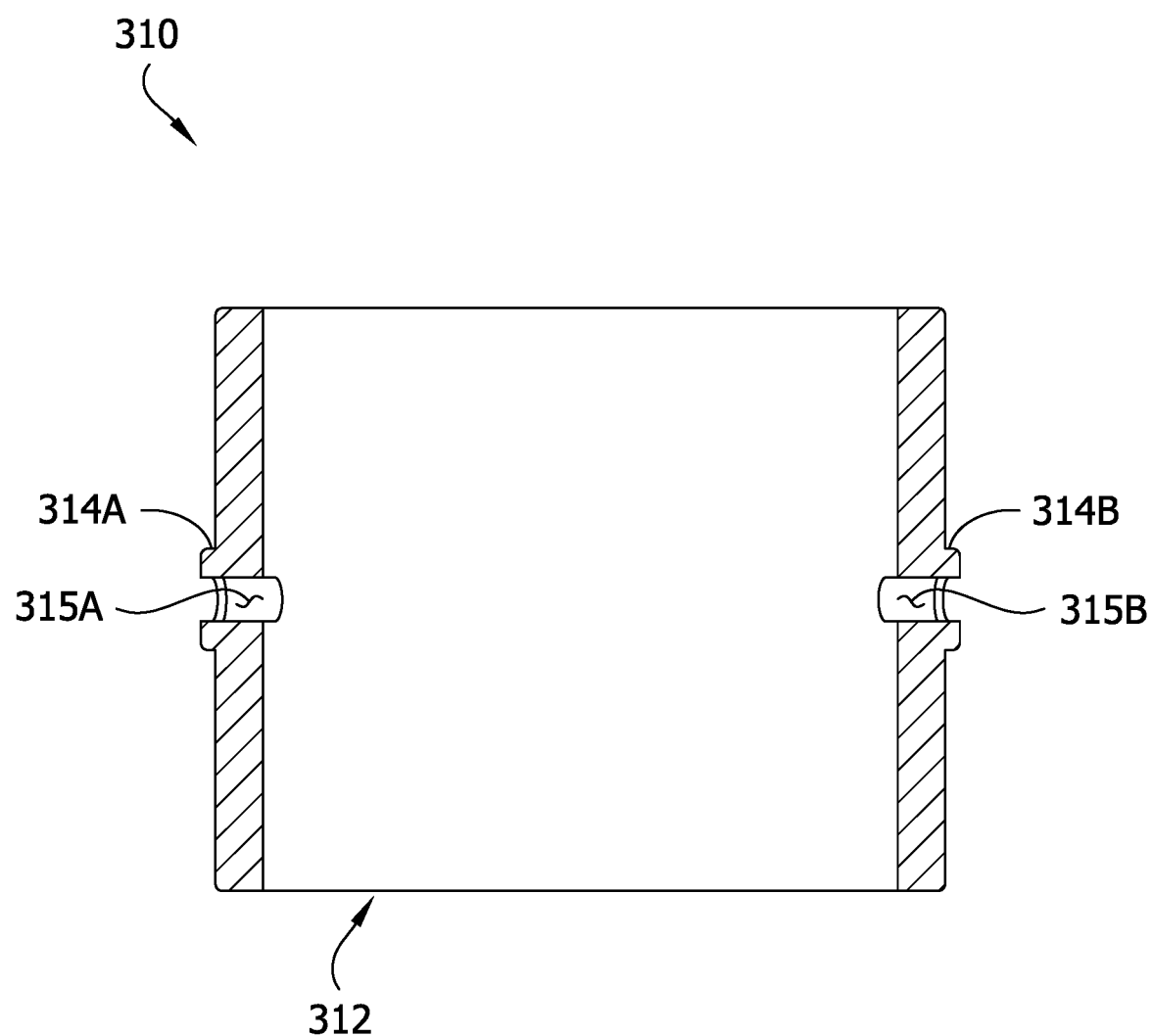
FIG. 16 is a cross section taken in the plane of line 16-16 of FIG. 14.

Referring to FIGS. 14-16, another embodiment of a tourniquet ring is generally indicated at 312. The ring 312 is adapted to impart an elastically compressive load on a body part B of a subject operative to restrict blood flow through the body part. The tourniquet ring 312 has a generally annular shape and comprises a top end, a bottom end, a generally annular interior side surface, and a generally annular exterior side surface. In the illustrated embodiment, corner edges between the top end and the interior and exterior side edges are chamfered. As above, the elastic ring 312 may be formed from any suitable elastic material such as silicone.

The ring 312 includes first and second reinforcing lugs 314A, 314B that are circumferentially spaced apart from one another at diametrically opposite sides of the ring in the illustrated embodiment. Each reinforcing lug 314A, 314B extends radially outward from an annular exterior surface of the ring 312. In the illustrated embodiment, each lug 314A, 314B is spaced apart between the top and bottom ends of the ring at about the same position along the height of the ring. More specifically, the lugs 314A, 314B are located about a midpoint of a height of the ring. When viewed in radially as shown in FIG. 14, the reinforcing lugs 314A, 314B have a generally obround shape comprising curved circumferential sides and relatively elongate, flat top and bottom ends. It is understood, however, that other reinforcing lugs could have other shapes or arrangements in other embodiments. In the illustrated embodiment, the reinforcing lugs 314A, 314B are formed integrally with the tourniquet ring 312 from a single piece of material. In other embodiments, the reinforcing lugs could be formed from a different material than the rest of the tourniquet ring (e.g., through co-injection molding as described above) and/or be separately attached the tourniquet ring.

Figure 19:
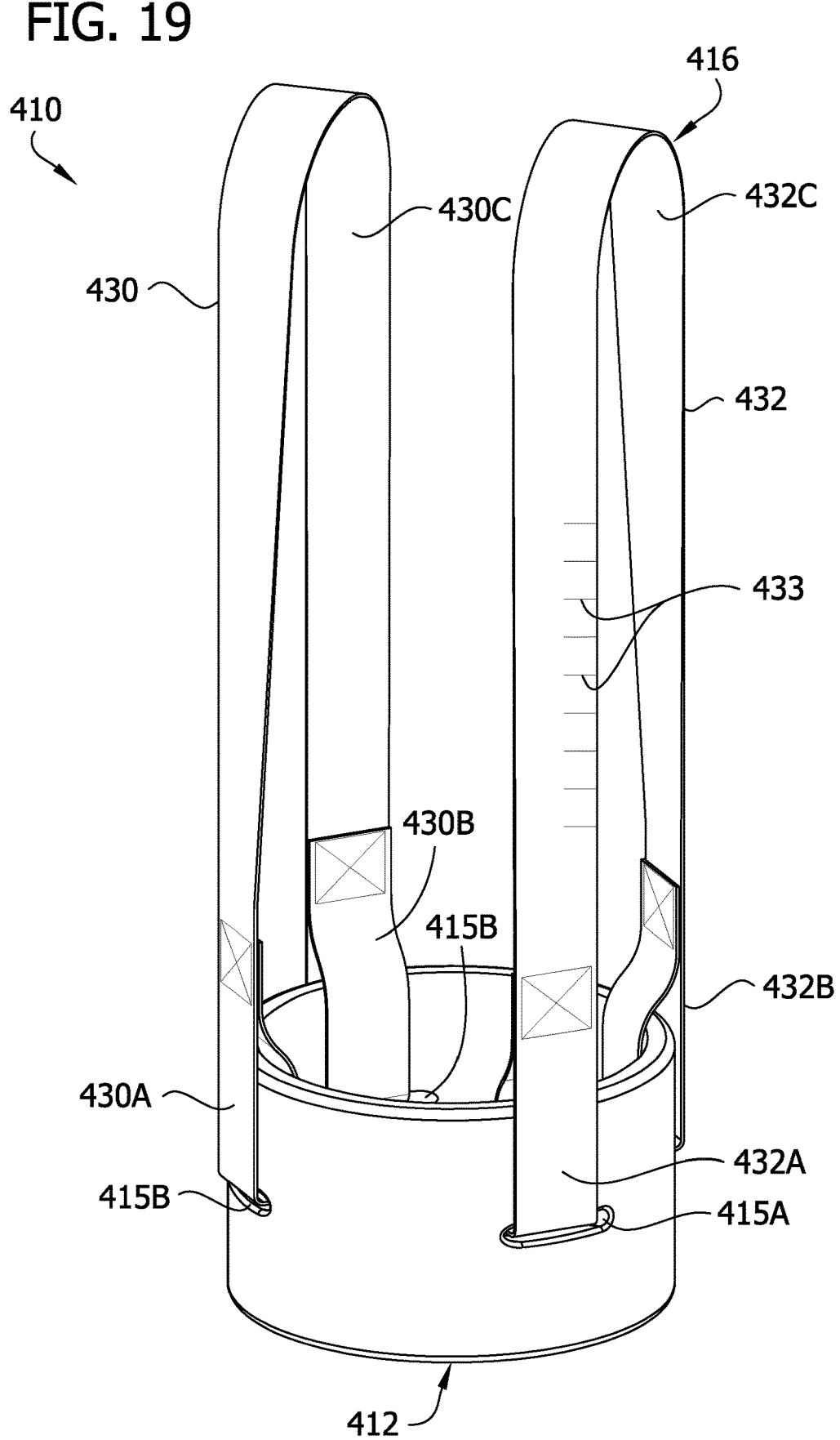
FIG. 19 is a perspective of another embodiment of a tourniquet.
Figure 20:
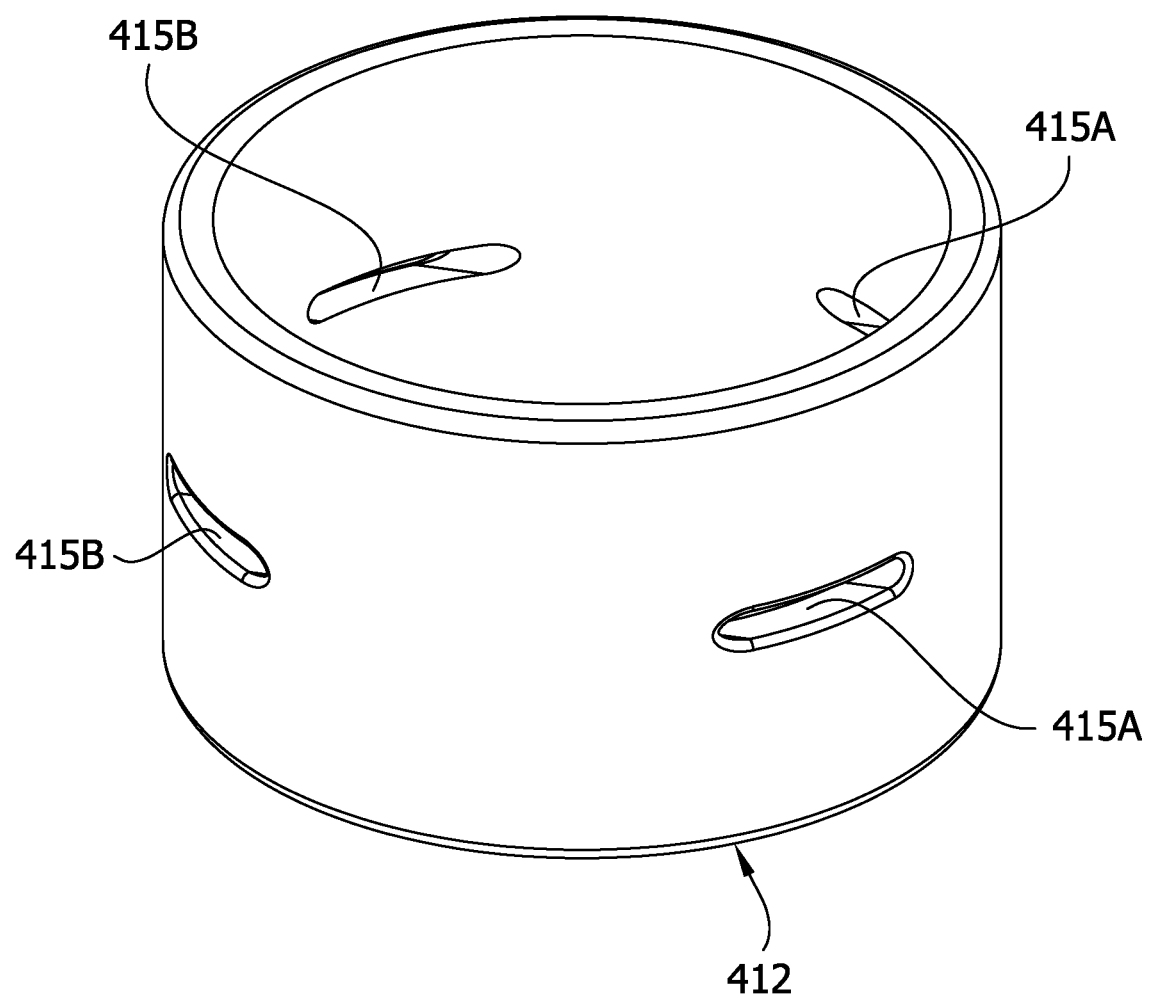
FIG. 20 is a perspective of a tourniquet ring of the tourniquet of FIG. 19.
Figure 21:
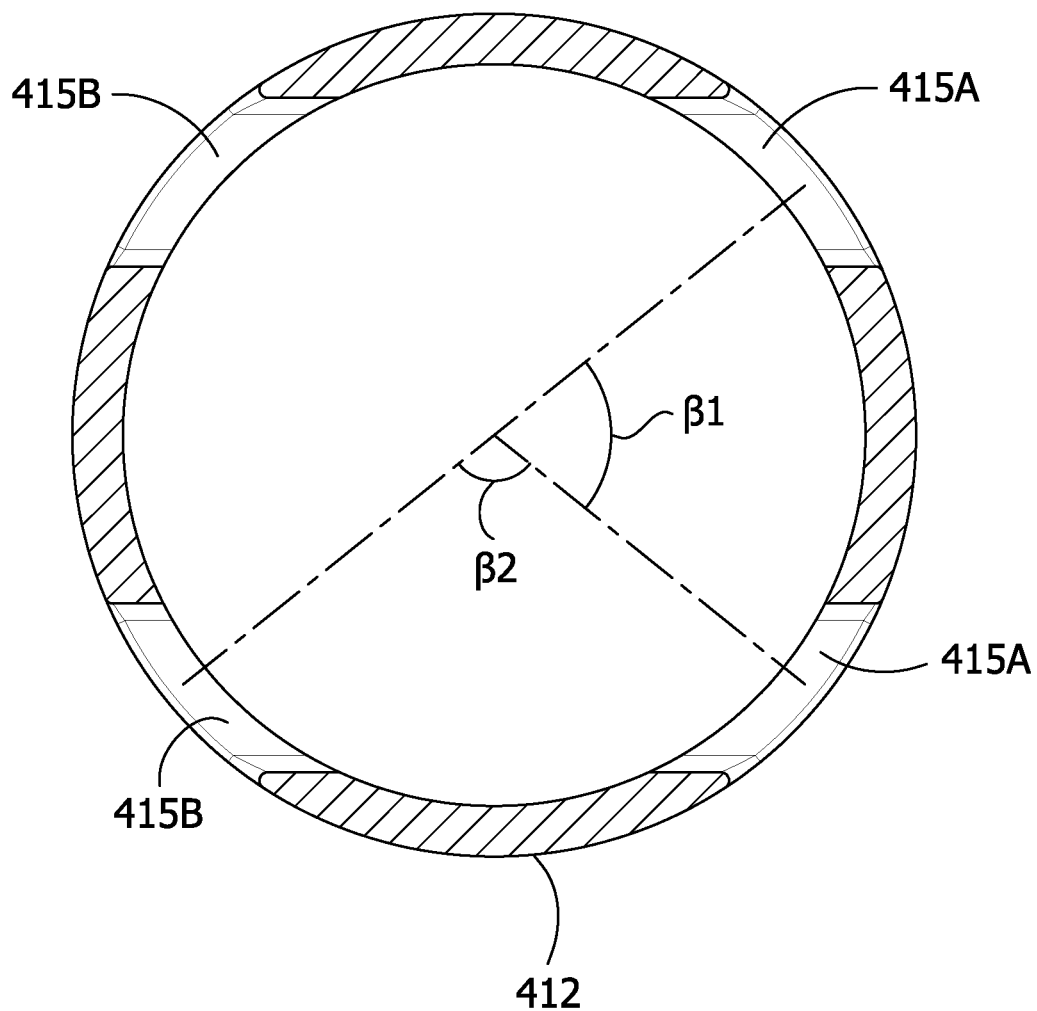
FIG. 21 is a section of the tourniquet ring of FIG. 20.

The tourniquet ring 312 defines first and second connection slots 315A, 315B that extend radially from the interior side surface through the exterior surface of the first and second lugs 314A, 314B, respectively. The connection slots 315A, 315B are substantially aligned with the lugs 314A, 314B. Thus in the illustrated embodiment, the connection slots 315A, 315B are located at diametrically opposite positions of the ring 312 and at about a midpoint along the height of the ring. Moreover, in the illustrated embodiment, each connection slot 315A, 315B has an obround shape that is slightly smaller than the obround shape of the respective reinforcing lug 314A, 314B. Each lug 314A, 314B extends circumferentially around and defines a portion of the respective slot 315A, 315B. The illustrated slots 315A, 315B are substantially centered on the respective lugs 314A 314B so that the lugs form rims around the slots having substantially uniform thicknesses about the slots. While each connection slot 315A, 315B is shown as a single oblong opening, multiple openings, for example, a pair of oblong openings 415A, 415B (FIGS. 19-21) could be used in place of each connection slot without departing from the scope of the disclosure. In one embodiment, centers of the openings 415A, 415B in each pair are spaced an angle β1 of between about 65 and about 75 degrees apart, and centers of adjacent openings in opposite pairs are spaced an angle β2 of between about 105 and about 115 degrees apart (FIG. 21). In one embodiment, centers of the openings 415A, 415B in each pair are spaced an angle β1 of about 70 degrees apart, and centers of adjacent openings in opposite pairs are spaced an angle β2 of about 110 degrees apart. The openings could have other spacing without departing from the scope of the disclosure. Additionally or alternatively, multiple opening having any shape, including round or oblong, could be spaced circumferentially around the tourniquet ring 312, 412. The openings could be arranged in pairs as shown in FIGS. 19-21 or uniformly spaced about the circumference. In one embodiment four openings are formed in the tourniquet ring 312, 412. However, a different number of openings could be used.

Figure 17:
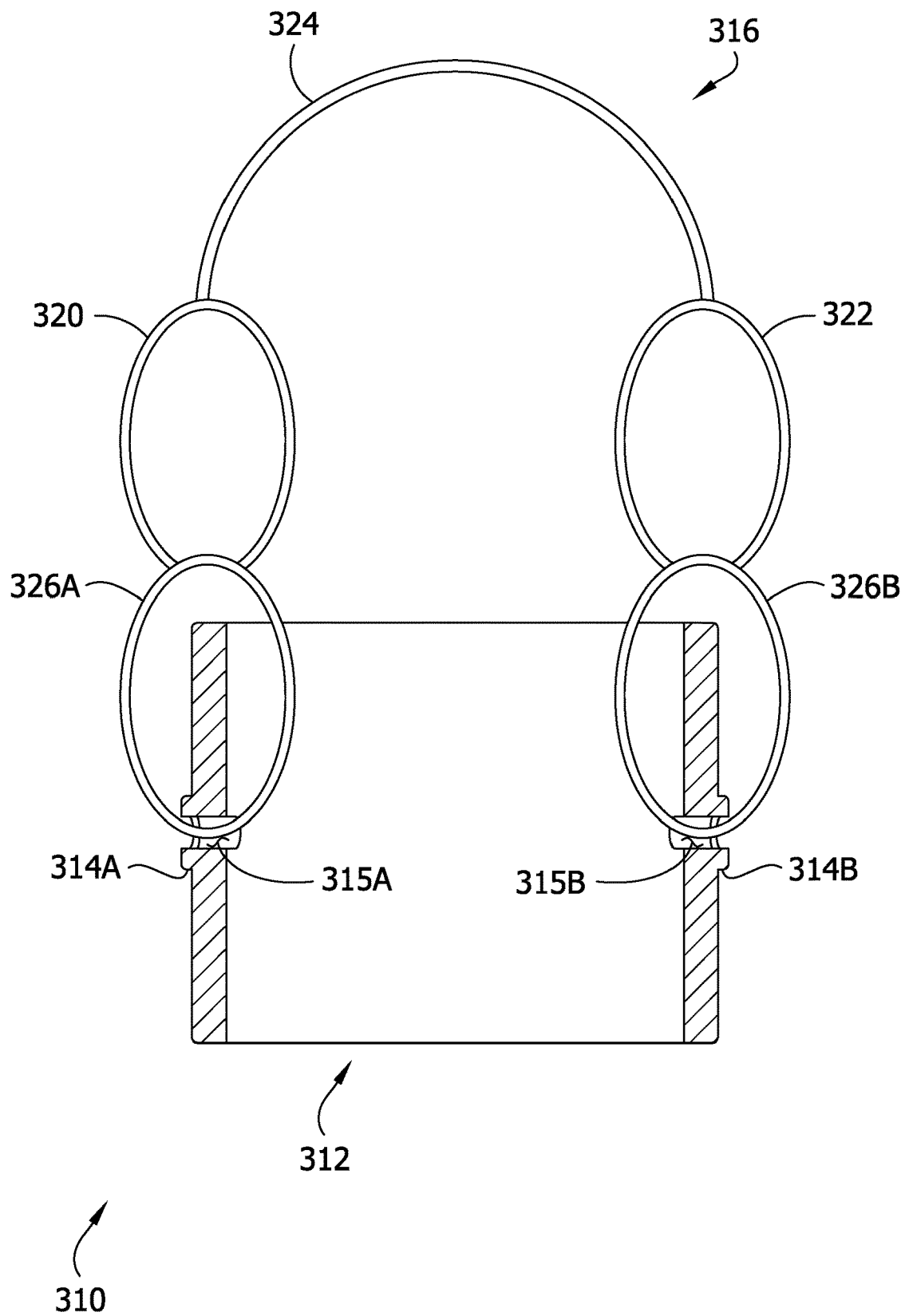
FIG. 17 is a cross section similar to FIG. 16, illustrating the tourniquet ring connected to a handle.

Referring to FIG. 17, the reinforcing lugs 314A, 314B and connection slots 315A, 315B are configured for securely connecting a handle 316 to the tourniquet ring 312. The handle 316 is substantially similar to handle 216. Like the handle 216, the handle 316 is formed from strips of pliable but substantially non-stretchable fabric arranged to form first and second loop straps 320, 322 and a connecting strap 324 extending between the loop straps that may be used to position the tourniquet 310 on the body part B. The handle 316 further includes first and second strap connection loops 3206A, 326B that are connected to the first and second loop straps 320, 322, respectively, for connecting the handle to the tourniquet ring 312. Each strap connection loop 326A, 326B extends through a connection respective slot 315A, 315B and extends circumferentially around the upper portion of the tourniquet ring 312 above the slot. The strip of fabric forming each connection loop 326A, 326B is fastened to itself adjacent the top end of the tourniquet ring 312 to secure the handle 316 to the tourniquet ring. It is understood that the handle 316 could include other connection structure that is received in the slots 315A, 315B to secure the handle to the tourniquet ring 312 in other embodiments. For example, in one or more embodiments, the loop straps 320, 322 could extend through the slots 315A, 315B to secure the handle 316 to the tourniquet ring 312.

In use, the handle 316 can be grasped using the loop straps 320, 322 or the connecting strap 324 as described above to pull the tourniquet ring 312 onto the body part B of the subject. In one or more embodiments, the tourniquet ring 312 slides uncovered along the body part B via lubrication applied directly to one of the body part and the interior side surface of the tourniquet ring. The lugs 314A, 314B transmit the pulling force from the handle 316 to the tourniquet ring 312 and provide reinforcement at locations where pulling forces are concentrated on the tourniquet 310.

Figure 18:
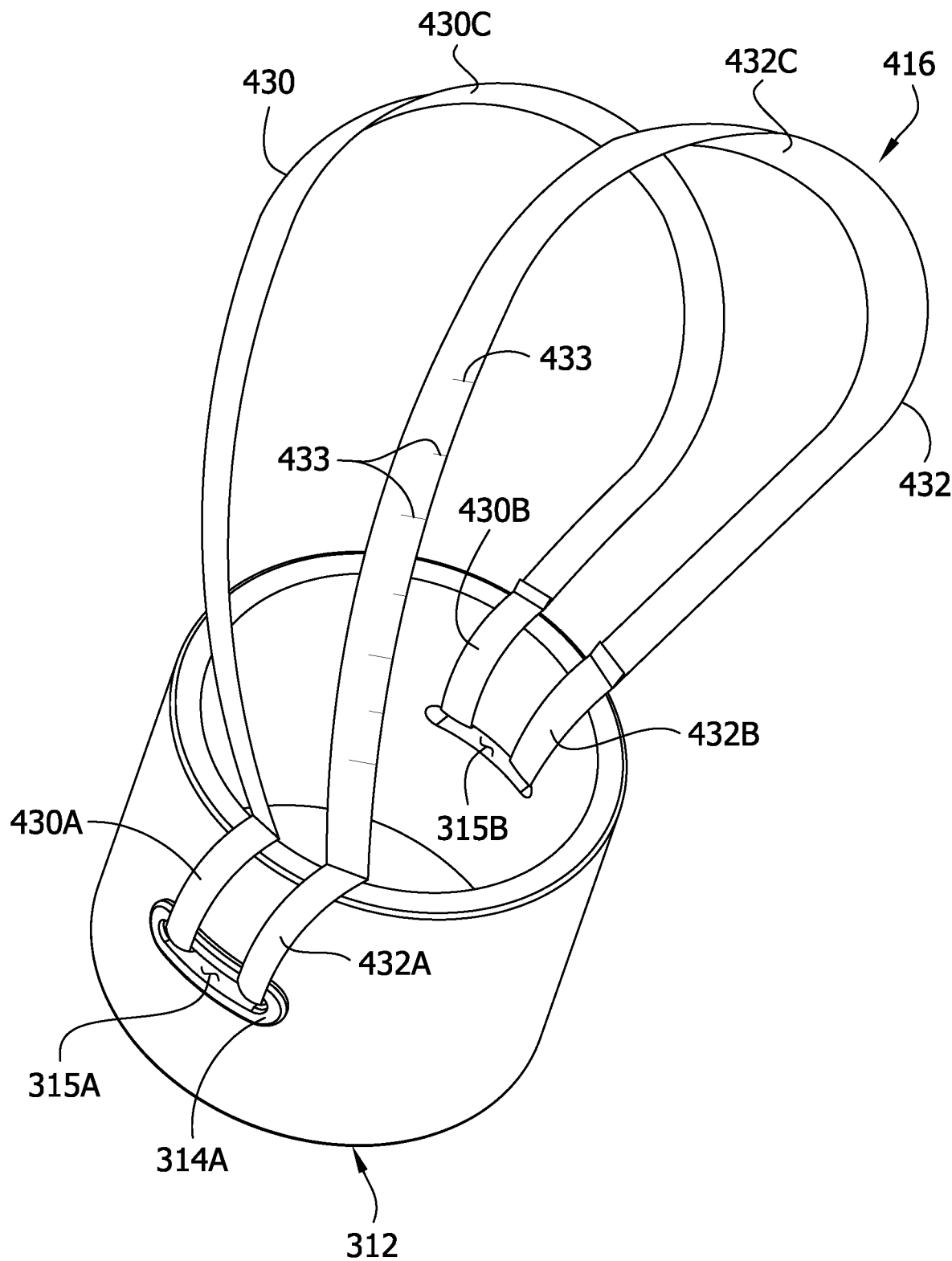
FIG. 18 is a perspective of the tourniquet ring of FIG. 14, illustrating the tourniquet ring connected to a handle.

Referring to FIG. 18, in another embodiment, the reinforcing lugs 314A, 314B and connection slots 315A, 315B are configured for securely connecting a handle, generally indicated at 416, to the tourniquet ring 312. The handle 416 comprises a first strap 430 and a separate second strap 432, which are about the same size in the illustrated embodiment. Each of the first and second straps has a first end secured to the tourniquet ring at the first connection slot 315A and a respective second end secured to the tourniquet ring at the second connection slot 315B. In the illustrated embodiment, the first strap 430 defines a first handle connection loop 430A at the first end thereof, a second handle connection loop 430B at a second end thereof, and a first handle portion 430C extending between the first and second handle loops. The second strap 432 defines a third handle connection loop 432A at the first end thereof, a fourth handle connection loop 432B at the second end thereof, and a second handle portion 432C extending between the first and second handle connection loops. The first handle connection loop 430A extends through a first end portion of the connection slot 315A and around the top end portion of the tourniquet ring 312 to secure the first end of the strap 430 to the tourniquet ring. The second handle connection loop 430B likewise extends through a first end portion of the connection slot 315B and around the top end portion of the tourniquet ring 312 to secure the second end of the strap 430 to the tourniquet ring. The first handle portion 430C curves between the first and second handle connection loops 430A, 430B to provide a first handle loop for grasping during use. The third handle connection loop 432A extends through a second end portion of the connection slot 315A and around the top end portion of the tourniquet ring 312 to secure the first end of the strap 432 to the tourniquet ring. The second handle connection loop 432B likewise extends through a second end portion of the connection slot 315B and around the top end portion of the tourniquet ring 312 to secure the second end of the strap 432 to the tourniquet ring. The second handle portion 432C curves between the first and second handle connection loops 430A, 430C to provide a second handle loop for grasping during use. The handle 416 could be used with tourniquet ring 412 as illustrated by tourniquet 410 shown in FIG. 19. In this embodiment, each connection loop 430A, 430B, 432A, 432B is received in a dedicated connection slot 415A, 415B. For example, connection loop 430A is received in one of connection slots 415B, connection loop 430B is received in the other of connection slots 415B, connection loop 432A is received in one of connection slots 415A, and connection loop 432B is received in the other of connection slots 415A.

In the illustrated embodiment, the strap 432 includes a plurality of measurement markings 433 for measuring the circumference of the body part of the user. Before use of the tourniquet ring 312, the handle portion 432C of the strap can be wrapped around the body part to measure the circumference of the body part. Suitably, either the strap 432 or the tourniquet ring 312 includes an indication of the range of body part circumferences for which the tourniquet ring is suitable for use. The measurement markings 433 can thus be used to determine whether the tourniquet ring 312 is properly sized for the subject body part prior to application.

To pull the tourniquet ring 312 onto the body part of the subject, the user can apply a lubricant to the body part as described above and then position the tourniquet ring on the end portion of the body part. In this position, the user grasps the first and second handle portions 430C, 432C and imparts a pulling force on each strap 430, 432. When two hands are available for pulling the tourniquet ring 312 onto the body part, the pulling force on each strap 430, 432 can be applied at an angle extending laterally outward away from the other strap. The first strap 430 conveys the pulling force to the tourniquet ring 312 at the first and second handle connection loops 430A, 430B adjacent the first end portions of the handle connection slots 315A, 315B. Similarly, the second strap 432 applies the pulling force to the tourniquet ring 312 at the third and fourth handle connection loops 432A, 432B adjacent to the second end portions of the handle connection slots 315A, 315B. The laterally outward component of the pulling force imparted on the straps 430, 432 causes the respective handle connection loops 430A, 430B, 432A, 432B to pull against the portions of the tourniquet ring 312 defining the slots 315A, 315B in opposite circumferential directions. Thus, a portion of the applied pulling force directly expands the tourniquet ring 312 to allow passage of the body part through the tourniquet ring as it is being pulled into position. It is understood that in other embodiments, the pulling force can be imparted on the handle 416 in other ways. For example, in one embodiment both straps 430, 432 can be grasped by the same hand during pulling.

In one embodiment, the tourniquet 310, 410 is removed from the subject's body part by applying a lateral pulling force to the handle 316, 416 to create space between the body part and the tourniquet ring 312, 412. The tourniquet is then severed from the subject's body part by locating a portion of a cutting implement (e.g., scissors or scalpel) between the tourniquet ring 312, 412 and the body part to cut the tourniquet ring from the body part. The tourniquets 10, 10', 110, 110', 210 of the other embodiments can be similarly removed.

OTHER STATEMENTS OF THE INVENTION

A. A non-pneumatic tourniquet comprising:
an annular cover;
at least one handle strap secured to the annular cover; and
a compression ring received in the annular cover comprising a band of resiliently elastic material extending circumferentially around a ring axis, the compression ring having a proximal end, a distal end, and a height extending between the proximal end and the distal end along the ring axis, the compression ring further having an inner surface, an outer surface, and a radial thickness extending between the inner and outer surfaces, the radial thickness being substantially uniform along the height of the compression ring.

B. A non-pneumatic tourniquet as set forth in claim A wherein the radial thickness is substantially uniform about the circumference of the compression ring;

C. A non-pneumatic tourniquet as set forth in claim A wherein the compression ring is seamless.

D. A non-pneumatic tourniquet comprising:
a compression ring comprising a band of resiliently elastic material extending circumferentially around a ring axis, the compression ring having a proximal end, a distal end, and a height extending between the proximal end and the distal end along the ring axis, the compression ring further having an inner surface, an outer surface, and a radial thickness extending between the inner and outer surfaces, and
a handle formed as one piece of material with the compression ring.

E. A non-pneumatic tourniquet as set forth in claim D wherein the compression and handle are formed from silicone.

F. A non-pneumatic tourniquet as set forth in claim D wherein the handle comprises a pair of handle projections extending radially outward from the compression ring.

G. A non-pneumatic tourniquet as set forth in claim D wherein the handle comprises a pair of handle projections extending axially from the compression ring.

H. A non-pneumatic tourniquet as set forth in either of claims F and G wherein each of the handle projections comprises at least one gripping formation configured to enhance gripping engagement.

It will be understood that a handle may be connected to a tourniquet ring in other ways in other embodiments. For example, ends of a handle may be separately attached to a tourniquet ring using an adhesive, a fastener, a welded joint, etc., without departing from the scope of the invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A method of exsanguinating a body part of a subject and constricting vessels of the body part to limit blood flow to the body part, the method comprising:
    manipulating a compression ring of a non-pneumatic tourniquet to position the compression ring over a distal end portion of the body part, the compression ring comprising a band of resiliently elastic material, the compression ring having a height extending between proximal and distal ends of the compression ring that is greater than a largest radial thickness of the compression ring; and
    applying a force to a handle of the tourniquet attached to the compression ring to slide the tourniquet proximally along the body part as the compression ring constricts around the body part to exsanguinate the body part and constrict vessels of the body part to prevent blood flow through the body part without changing an axial orientation of the compression ring such that the compression ring does not roll along the body part, the handle being attached directly to the compression ring and formed integrally with the compression ring from one piece of material.

2. A method as set forth in claim 1 further comprising applying a lubricant to one of the body part of the subject and the tourniquet before the step of applying the force.

3. A method as set forth in claim 1 wherein the compression ring is slid along the body without using lubricant.

4. A method as set forth in claim 3 wherein the compression ring is formed from silicone.

5. A method as set forth in claim 4 wherein the compression ring comprises an uncovered elastic ring.

6. A method as set forth in claim 1 wherein the step of applying a force to the handle comprises one of pulling and pushing the compression ring using the handle to locate the tourniquet at a selected location on the subject's body part.

7. A method as set forth in claim 6 further comprising removing the tourniquet from the subject's body part by applying force to the handle to create space between the body part and the tourniquet allowing the tourniquet to be severed from the body part.

8. A method as set forth in claim 7 further comprising severing the tourniquet from the subject's body part by locating a portion of a cutting implement between the compression ring and the body part to cut the compression ring from the body part.

9. A method as set forth in claim 6 wherein the step of pulling and pushing the compression ring using the handle comprises separately grasping first and second straps.

10. A method as set forth in claim 1 wherein the band is flat.

11. A method as set forth in claim 1, wherein the body part is an arm.

* * * * *